United States Patent
Jevtic et al.

(10) Patent No.: US 9,491,841 B2
(45) Date of Patent: Nov. 8, 2016

(54) PLASMA GENERATOR USING DIELECTRIC RESONATOR

(71) Applicant: Radom Corporation, West Allis, WI (US)

(72) Inventors: Jovan Jevtic, West Allis, WI (US); Ashok Menon, Shorewood, WI (US); Velibor Pikelja, Milwaukee, WI (US)

(73) Assignee: Radom Corporation, West Allis, WI (US)

( * ) Notice: Subject to any disclaimer, the term of this patent is extended or adjusted under 35 U.S.C. 154(b) by 0 days.

(21) Appl. No.: 14/775,492

(22) PCT Filed: Mar. 12, 2014

(86) PCT No.: PCT/US2014/024306
§ 371 (c)(1),
(2) Date: Sep. 11, 2015

(87) PCT Pub. No.: WO2014/159588
PCT Pub. Date: Oct. 2, 2014

(65) Prior Publication Data
US 2016/0029472 A1    Jan. 28, 2016

Related U.S. Application Data

(60) Provisional application No. 61/779,557, filed on Mar. 13, 2013.

(51) Int. Cl.
*H05H 1/46* (2006.01)
*G01N 22/00* (2006.01)
*H01J 49/10* (2006.01)

(52) U.S. Cl.
CPC ............... *H05H 1/46* (2013.01); *G01N 22/00* (2013.01); *H01J 49/10* (2013.01); *H05H 2001/4652* (2013.01); *H05H 2001/4682* (2013.01)

(58) Field of Classification Search
CPC ........ H05H 1/46; H05H 1/24; H05H 1/2406; H05H 1/30; H01J 49/10; H01J 49/105; H01J 37/08; G01J 1/42; G01J 3/443
USPC ........ 250/288, 215, 423 R, 424; 219/121.48, 219/121.52, 121.44; 315/111.21, 111.81, 315/39; 324/318, 633
See application file for complete search history.

(56) References Cited

U.S. PATENT DOCUMENTS 4,778,561 A * 10/1988 Ghanbari ................ H01J 37/08
                                                                    118/50.1
5,517,157 A    5/1996 English
(Continued)

FOREIGN PATENT DOCUMENTS

JP    2003273615         9/2003
JP    2004349199 A      12/2004
(Continued)

OTHER PUBLICATIONS

The ISR & Written Opinion from PCT/US2014/024306: Filed: Mar. 12, 2014.
(Continued)

*Primary Examiner* — David A Vanore
(74) *Attorney, Agent, or Firm* — Boyle Fredrickson, S.C.

(57) ABSTRACT

A dielectric resonator is excited at its natural resonant frequency to produce highly uniform electric field for the generation of plasma. The plasma may be used optical or mass spectrometer.

19 Claims, 27 Drawing Sheets

(56) References Cited

U.S. PATENT DOCUMENTS

| | | | |
|---|---|---|---|
| 6,265,717 | B1 | 7/2001 | Sakata et al. |
| 8,031,824 | B2 * | 10/2011 | Bystriskii ............... G21B 1/052 376/107 |
| 2003/0086840 | A1 | 5/2003 | Himori et al. |
| 2003/0160956 | A1 | 8/2003 | Chevalier |
| 2004/0164682 | A1 | 8/2004 | Hopwood et al. |
| 2005/0093023 | A1 * | 5/2005 | Raspopin ............... B82Y 20/00 257/202 |
| 2006/0137613 | A1 | 6/2006 | Kasai |
| 2006/0197529 | A1 * | 9/2006 | Geifman ............... C04B 35/495 324/316 |
| 2007/0075051 | A1 | 4/2007 | Morrisroe |
| 2007/0229808 | A1 * | 10/2007 | Kondo ................ H05H 1/2406 356/237.1 |
| 2007/0229819 | A1 | 10/2007 | Seaward et al. |
| 2009/0045749 | A1 | 2/2009 | Ganachev et al. |
| 2010/0320379 | A1 | 12/2010 | Morrisroe |
| 2011/0000780 | A1 | 1/2011 | Tian et al. |
| 2011/0079505 | A1 | 4/2011 | White et al. |
| 2013/0063863 | A1 * | 3/2013 | Timler ................ F28D 15/0266 361/313 |
| 2016/0025656 | A1 * | 1/2016 | Jevtic ....................... H05H 1/46 324/633 |
| 2016/0029472 | A1 * | 1/2016 | Jevtic ....................... H05H 1/46 250/288 |

FOREIGN PATENT DOCUMENTS

| | | |
|---|---|---|
| JP | 2006185923 A | 7/2006 |
| JP | 2009272127 A | 11/2009 |
| KR | 1020090112360 A | 10/2009 |

OTHER PUBLICATIONS

The ISR & Written Opinion from PCT/US2014/024312; Filed: Mar. 13, 2014.

Singapore Search Report & Written Opinion of Singapore Application No. 11201507580U.

Singapore Search Report & Written Opinion of Singapore Application No. 11201507579U.

EP Supplementary Search Report of Application No. 14772720.0 dated Aug. 24, 2016.

EP Supplementary Search Report of Application No. 14776018.5 dated Aug. 24, 2016.

* cited by examiner

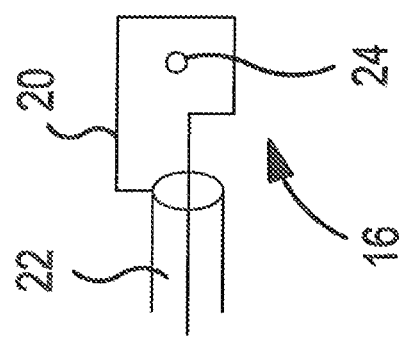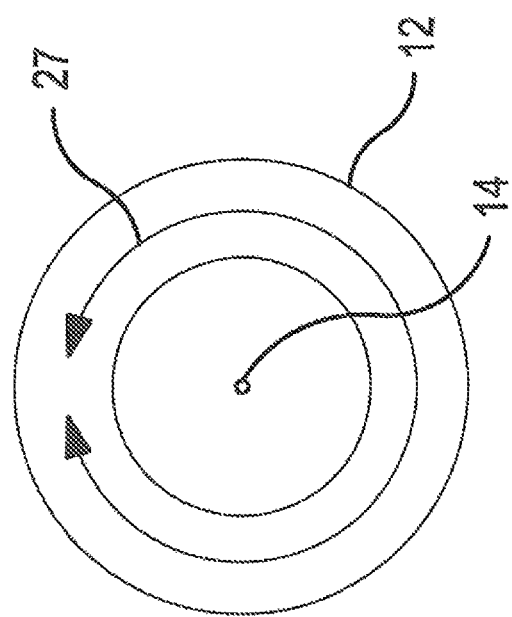
FIG. 2

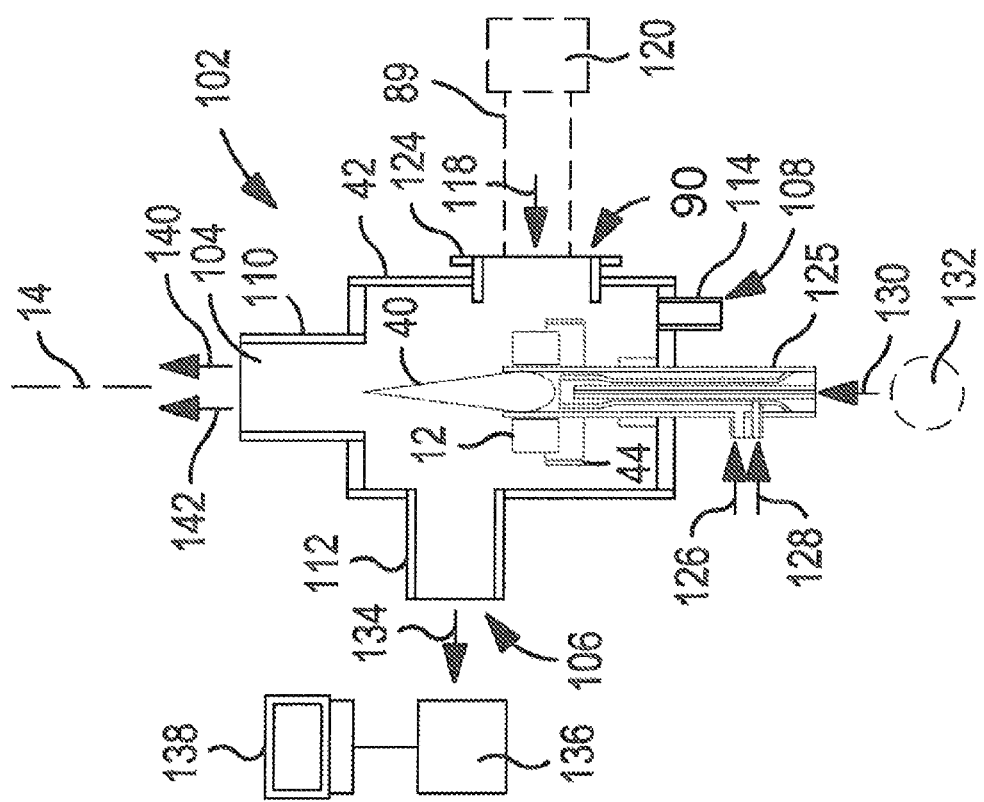

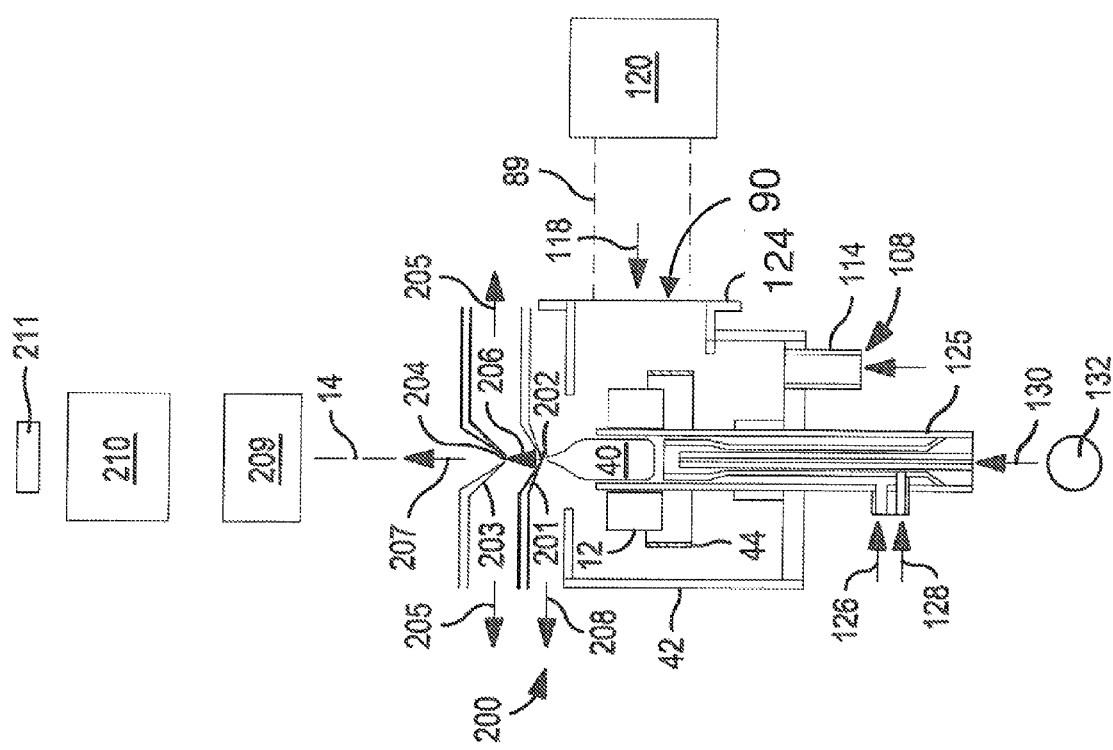

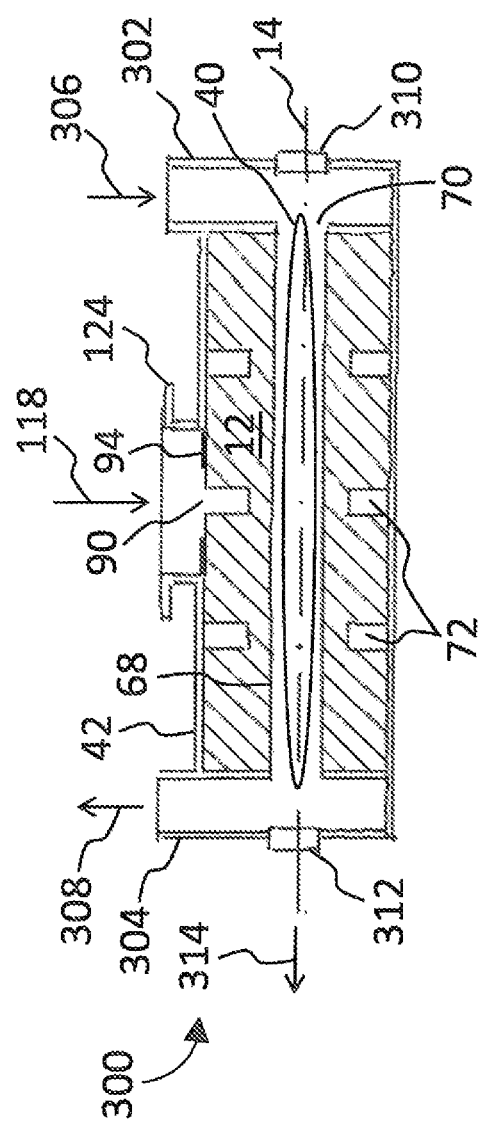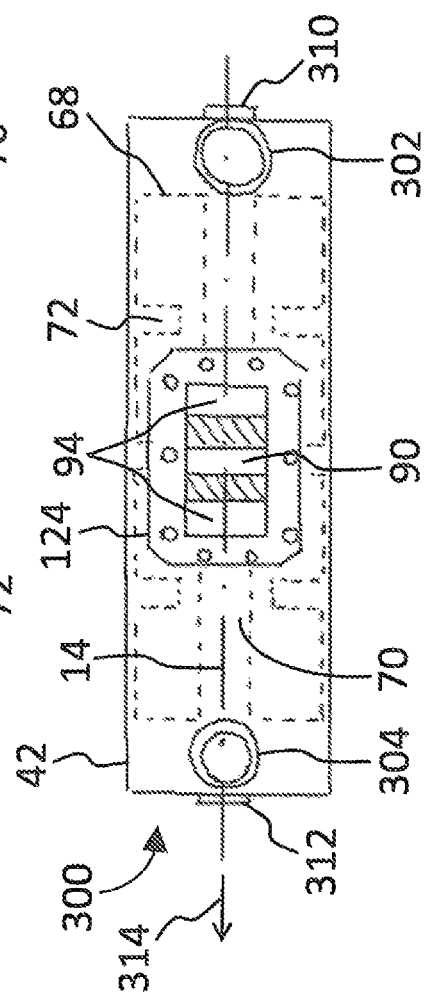

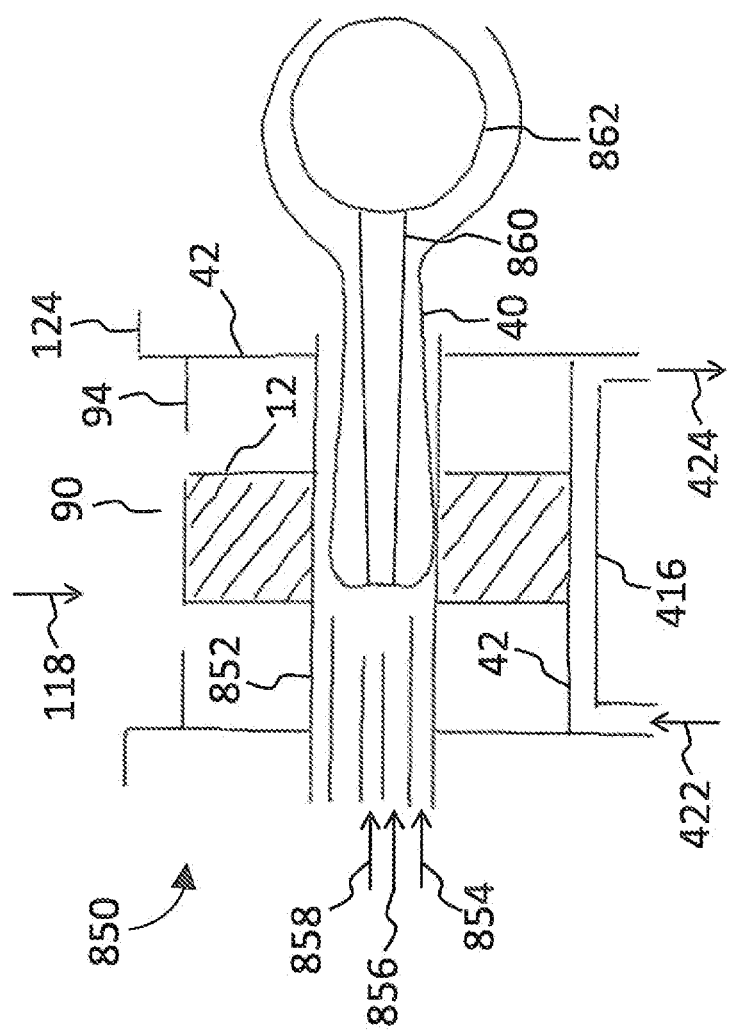

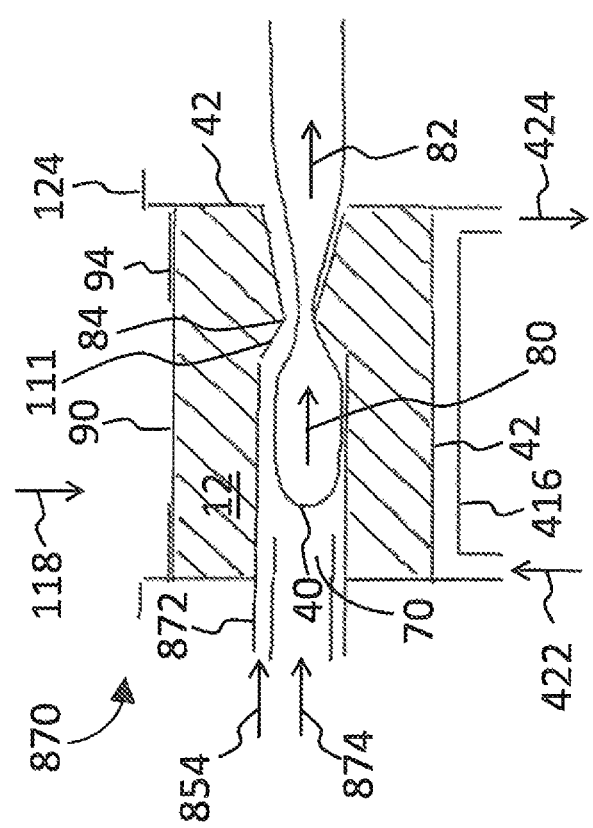

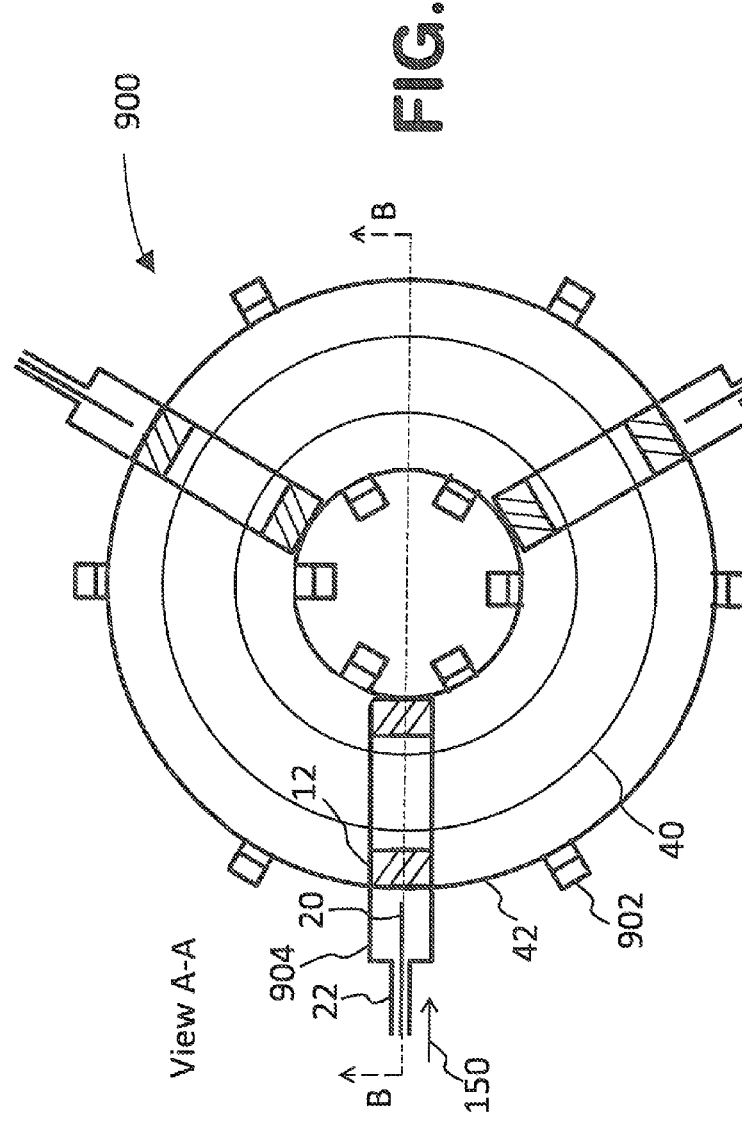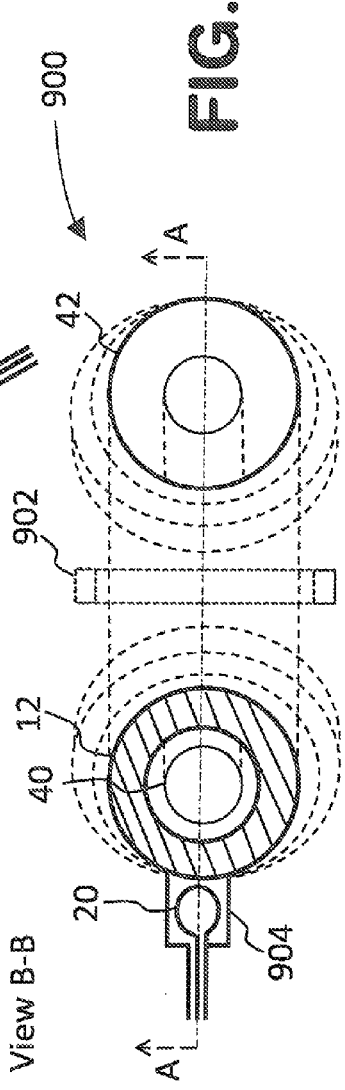
FIG. 27a
FIG. 27b

PLASMA GENERATOR USING DIELECTRIC RESONATOR

CROSS REFERENCE TO RELATED APPLICATION

This application claims the benefit of U.S. provisional application 61/779,557 filed 13 Mar. 2013 and hereby incorporated by reference.

BACKGROUND OF THE INVENTION

The present invention relates generally to electrical antennas and in particular to an antenna generating an efficient and uniform electromagnetic field for plasma generation and the like.

High frequency electrical fields for the generation of plasma may make use of a conductive coil ("field applicator") driven by an AC current oscillating in the megahertz to gigahertz range. A gas within the coil receives energy from the coil through inductive coupling exciting the gas into a plasma state.

Such inductive coupling techniques for generating plasma have a number of significant problems. First, normally the conductive coil must have multiple "turns" and each turn exhibits a mutual capacitance with adjacent turns of the loop creating field (and hence plasma) manifest as of nonuniform plasma ion speeds, trajectories and densities. Non-uniformities in the plasma may adversely affect applications were uniform plasma is required (for example, for etching in the integrated circuit industry) and may waste energy on undesired plasma processes. The mutual capacitance also limits the voltage that may be applied to the conductive coil without dielectric breakdown between the turns of the coil.

Second, the large amount of electrical power and hence large amounts of electrical current required to pass through the conductive coil produce significant resistive heating requiring complicated or bulky cooling structures. The use of highly conductive materials, such as copper, can reduce resistive losses, but the use of copper and similar metals is complicated by the susceptibility of such highly conductive materials to corrosion and melting in the harsh environment of the plasma.

Third, efficient driving of the conductive loop requires that the loop be part of a resonant structure implemented by placing a tuning capacitor into the coil circuit. Capacitors suitable for this purpose are expensive and bulky.

SUMMARY OF THE INVENTION

The present invention provides an antenna structure for generating plasma by using a dielectric antenna. The present inventors have determined that such antennas when fabricated with the material having high dielectric constant and low dielectric losses can be operated at resonance to provide for high field strengths with low power dissipation.

While the inventors do not wish to be bound by a particular theory, it is understood that the invention replaces "conduction" current of electrons in a conventional coil with "polarization" current of electrons in the dielectric material. The polarization current is due to the minor displacement of elementary charges bound to molecules of the dielectric material under the influence of an electric field. Both types of current (conduction current and polarization current) produce a magnetic field and an induced electric field according to the same laws of electromagnetism. However, since the dielectric material is at once its own capacitor and an inductor, the electric-potential is exactly zero everywhere inside the dielectric and in the space around the dielectric. Parasitic capacitive coupling is therefore entirely eliminated and the electric field is produced solely by induction. It is further believed that improved current distribution is obtained through lack of "skin" effects in the dielectric material that cause conductive current flow, unlike polarization current, to concentrate in the outermost portions of a ring structure.

Specifically then, the present invention provides a plasma generator having a dielectric resonator structure having a central axis and a radiofrequency power source electrically coupled to the dielectric resonator structure to promote an alternating polarization current flow at a natural resonant frequency of the dielectric resonator structure about the axis to generate plasma in an adjacent gas.

It is thus a feature of at least one embodiment of the invention to provide an improved radiofrequency antenna for the generation of intense but uniform electrical fields for plasma production.

The dielectric resonator may have any one or more of the qualities of: a quality factor of greater than 100, an electrical resistivity greater than $1 \times 10^{10}$ Ω·cm, a dielectric constant with a loss tangent of less than 0.01, and a dielectric constant greater than five It is thus a feature of at least one embodiment of the invention to provide a dielectric material that produces extremely low losses at radiofrequency fields and high power levels to minimize problems of cooling and energy loss.

The dielectric resonator may be of a material having melting point greater than a melting point of copper.

It is thus a feature of at least one embodiment of the invention to provide a material that is robust against the extremely high temperatures of plasma.

The dielectric material may, for example, be alumina ($Al_2O_3$) or calcium titanate ($CaTiO_3$).

It is thus a feature of at least one embodiment of the invention to provide an apparatus that may be constructed of relatively common and manufacturable materials.

The dielectric resonator may be a ring having a central opening along the axis.

It is thus a feature of at least one embodiment of the invention to provide a dielectric resonator that is relatively simple to manufacture.

The ring may have a central opening of at least one millimeter diameter or at least one half inch.

It is thus a feature of at least one embodiment of the invention to provide a dielectric resonator that is readily adaptable to forming plasma in flowing gas.

To that end, the plasma generator may include a gas port introducing gas into the ring along an axis of the ring.

It is thus a feature of at least one embodiment of the invention to provide the elements of a plasma torch for spectroscopic or other applications.

The radiofrequency power source may automatically seek the natural resonant frequency of the dielectric resonator structure to output radiofrequency power at the natural resonant frequency of the dielectric resonator structure.

It is thus a feature of at least one embodiment, of the invention to provide a plasma generator that may automatically adjust to variations in the dielectric resonant material or its environment.

The radiofrequency power source may be a magnetron or a solid-state or vacuum tube oscillator.

It is thus a feature of at least one embodiment of the invention to permit the generation of extremely high frequency plasma.

These particular objects and advantages may apply to only some embodiments falling within the claims and thus do not define the scope of the invention.

BRIEF DESCRIPTION OF THE DRAWINGS

FIG. 2 is a top plan view of the ring dielectric resonator of FIG. 1 showing the orientation of polarization current flow;

FIG. 17 is a simplified cross-sectional view of a spectrometer incorporating the dielectric resonator of the present invention;

FIG. 18 is a simplified schematic cross-sectional view of a mass spectrometer incorporating the dielectric resonator of the present invention.

FIGS. 19a and 19b are simplified cross-sectional views of compact microwave gas discharge lasers using the plasma system of the present invention;

FIG. 25 is a simplified cross-sectional view of a microwave plasma torch using the present invention;

FIG. 26 is a simplified cross-sectional view of a microwave plasma torch such as may form the basis of a rocket engine;

FIGS. 27a and 27b are top plan and side elevational cross-sectional views of an ion cyclotron resonance plasma heating system.

DETAILED DESCRIPTION OF THE PREFERRED EMBODIMENT

Figure 1:
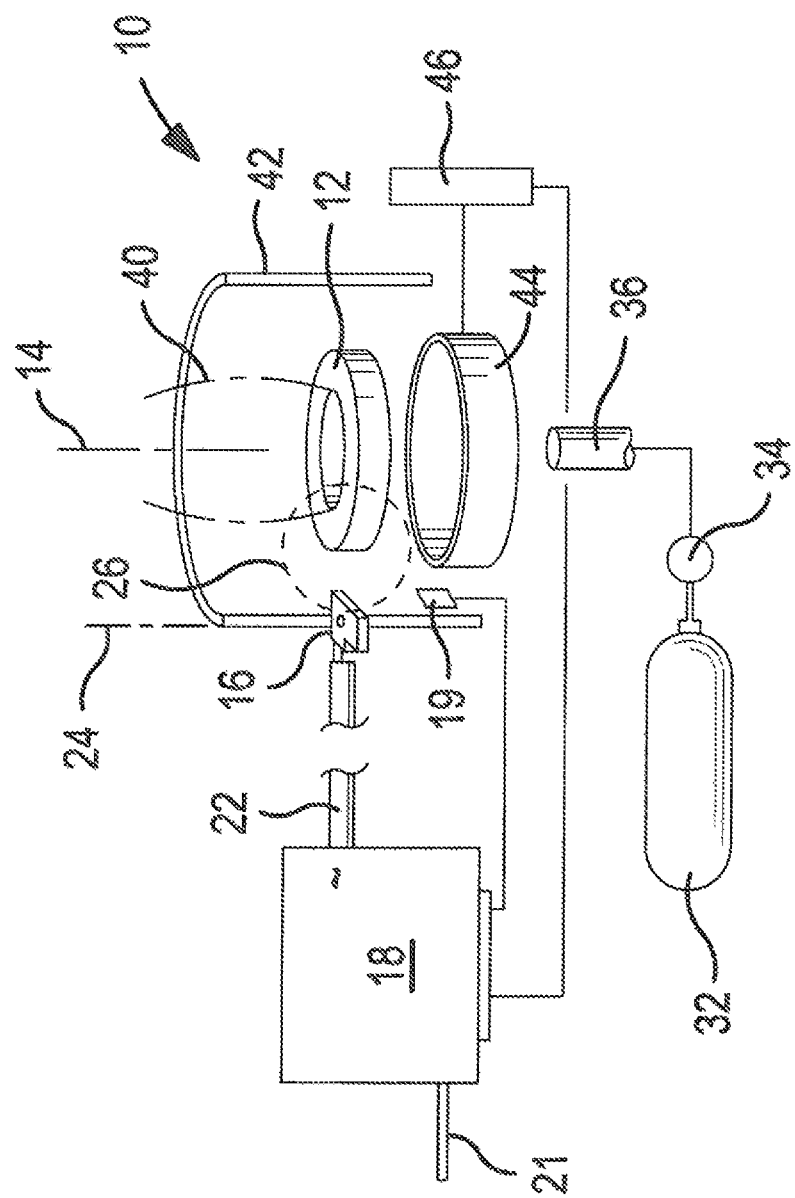
FIG. 1 is a partial cutaway perspective view of a plasma generator using a ring dielectric resonator of one embodiment of the present invention.

Referring now to FIG. 1, a plasma generator 10 of the present invention may provide for a dielectric resonator 12 being in this embodiment a cylindrical annulus centered about an axis 14.

As is understood in the art, dielectric materials are substantially insulators with respect to direct currents (that is when a dielectric is placed in an electric field electrical charges do not flow freely through the material as they do in a conductor) but can provide for polarization currents produced by slight shifts in the equilibrium positions of bound electrons or ions in the material.

In this embodiment, the dielectric resonator 12 may be made of alumina ($Al_2O_3$) and may be a circular annulus or ring being two inches in outer diameter, one inch in inner diameter and 0.75 inches in length along axis 14 and having an electrical resonance at approximately 2.45 gigahertz. This material exhibits a quality factor of greater than 5000, a relative dielectric constant of 9.8 and retains its electrical properties and physical integrity at temperatures exceeding 1000 degrees centigrade.

An alternative material for the dielectric resonator 12 may be calcium titanate ($CaTiO_3$) being 3.13 inches in outer diameter 2.34 inches in inner diameter and 1.12 inches in length and resonating at approximately 430 megahertz. This ring exhibits a quality factor in excess of 5000 and has a relative dielectric constant of 200.

Many types of advanced technical ceramics meet these requirements, but other dielectric materials with similar electrical properties may be used instead.

More generally, the dielectric material of the dielectric resonator 12 may have the following properties: (a) loss tangent less than 0.01, (b) quality factor greater than 100, (c) relative dielectric constant larger than 5. Alternatively quality factor should be greater than 1000.

Desirably the dielectric material may have a resistivity greater than $1 \times 10^{10}$ ohm centimeters and typically greater than $1 \times 10^{14}$ ohm centimeters. Desirably, the dielectric material may have a melting point higher than copper or other comparable conductive metals. The dielectric constant is preferably greater than five and more desirably greater than nine. These examples are not intended to be limiting.

The resonant frequency of a ring is approximately inversely proportional to the square root of the relative dielectric constant and approximately inversely proportional to the linear size of the ring, if all three dimensions of the ring are changed by the same factor, allowing these examples to be readily modified to other dimensions.

The dielectric resonator 12 may be positioned near a coupling antenna 16 in turn attached to a radio frequency power supply 18 the latter producing a high frequency electrical current exciting the coupling antenna 16 at the resonant frequency of the dielectric resonator 12. Matching of the frequency output of the radiofrequency power supply 18 to the resonant frequency of the dielectric resonator 12 may be done manually by adjusting a frequency setting, or automatically, for example, by using a feedback system detecting impedance changes associated with resonance. Automatic tuning may also be provided by "self resonance" using feedback from a sensing antenna 19 whose output drives the radiofrequency power supply 18 acting as an amplifier. Self resonance is provided by ensuring a necessary loop phase shift as is generally understood in the art. The radiofrequency power supply 18 receives electrical power 21, for example, line current from a conventional source.

The radiofrequency power source may be electrically coupled to the dielectric resonator. As a magnetic field is also present, the radiofrequency power source can be both electrically coupled and magnetically coupled to dielectric resonator structure; hence the radiofrequency power source may be said to be electromagnetically coupled to the dielectric resonator structure. The coupling promotes an alternating polarization current flow at a natural resonant frequency of the dielectric resonator structure. Generally, the radiofrequency power source is driven at a frequency or a range of frequencies (such as broadband) which is sufficient to couple at least some power into the dielectric resonator structure at its natural resonant frequency. Preferably the radiofrequency power source is driven at a frequency which is related to the natural resonant frequency of the dielectric resonator structure. More preferably the radiofrequency power source is driven at a frequency which is within two full width at half maximum (FWHM) bandwidths of the resonant frequency of the dielectric resonator structure when the resonator is loaded. The bandwidth of an unloaded dielectric resonator is very narrow and may broaden by a factor of 100 when loaded with the plasma.

Figure 14:
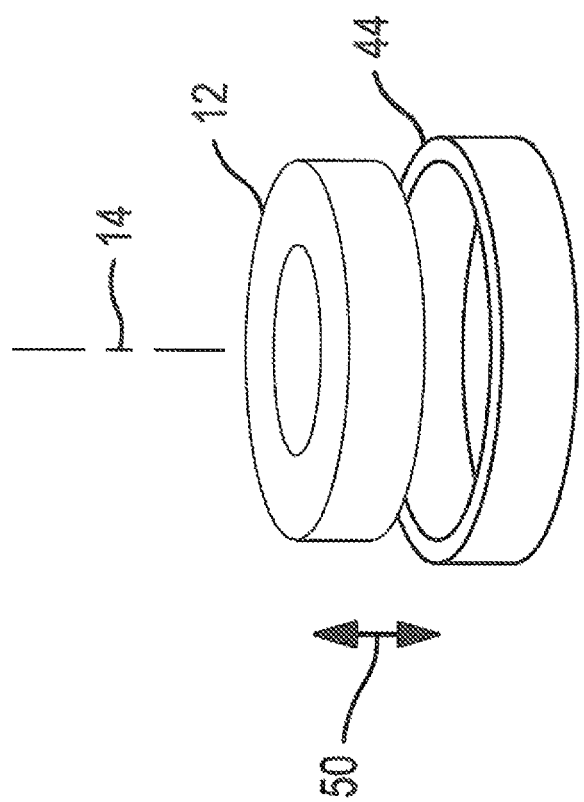
FIG. 14 is a figure similar to FIG. 13 showing alternative tuning structure in which one dielectric resonator may fit over the other dielectric resonator for tuning.

Referring now to FIGS. 1 and 14, the resonant frequency of the dielectric resonator 12 may be adjusted not only by changing the dimensions of the dielectric resonator 12 but by placing a second dielectric tuning, element 44 in proximity to the dielectric resonator 12. In this example of FIG. 14, the tuning element 44 is a cylindrical annulus larger than the outer diameter of the dielectric resonator 12 and aligned with axis 14. The tuning element 44 is attached to a mechanism 46 (for example, a rack and pinion lead screw or the like) allowing it to be moved along the axis as indicated by movement arrow 50 to change the inductive coupling between tuning element 44 and dielectric resonator 12 thereby changing the resonant frequency of dielectric resonator 12. Because tuning element 44 may fit around dielectric resonator 12 close coupling may be established for sensitive tuning. The movement of the tuning elements 44 may be manual or automatic according to feedback control, for example, according to sense impedance as described above.

Figure 13:
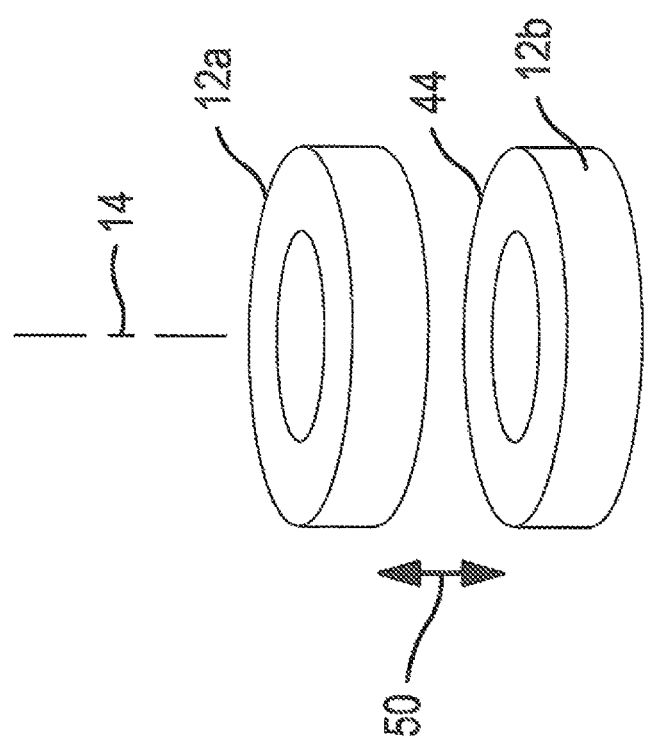
FIG. 13 is a perspective view of two identical ring-shaped dielectric resonators movable with respect to each other for tuning.

Referring now to FIG. 13, in an alternative embodiment, two identical dielectric resonators 12a and 12b may be used with dielectric resonator 12b acting as tuning element 44. The use of two identical components provides greatly increased tuning range and an extended region of uniform electrical field. One or both of the dielectric resonator 12a and dielectric resonator 12b may provide for electrical fields generating plasma.

Alternatively, in either of the above examples, the tuning elements 44 may be a metal such as aluminum, copper, or silverplated copper to provide similar tuning effects.

Figure 11:
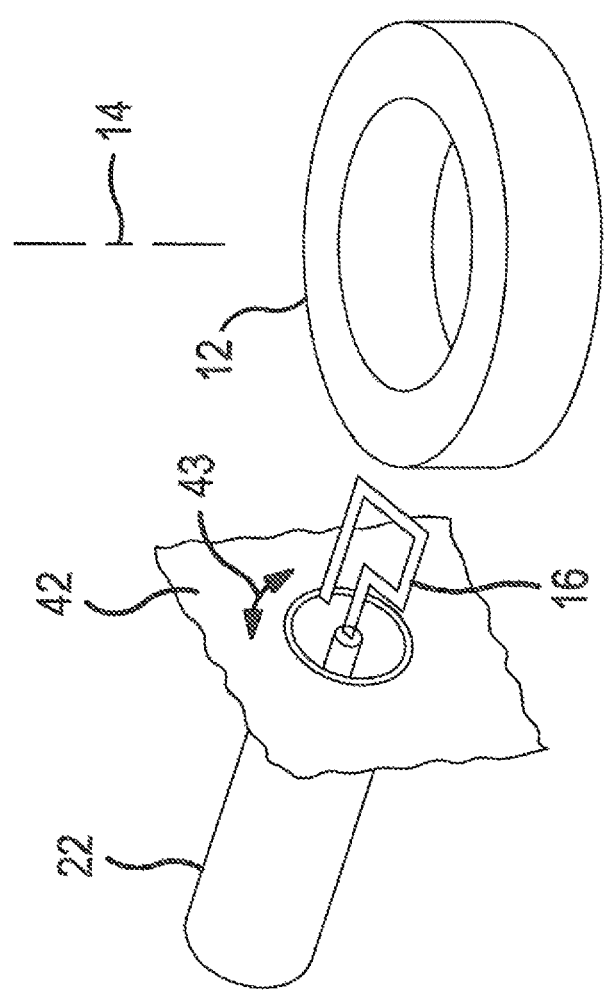
FIG. 11 is a fragmentary view of a loop power coupling system similar to that shown in FIG. 1 for inductively coupling electrical power into the dielectric resonator.

Referring also to FIGS. 2 and 11, in this example, the coupling antenna 16 may be a single loop 20 terminating a coaxial cable 22 leading to the power supply 18 and having an axis 24 generally parallel to axis 14 to couple electrical power inductively between the loop 20 and the dielectric resonator 12 with magnetic flux lines 26. The single loop 20 may be adjusted as indicated by rotation arrow 43 to control the degree of coupling and to provide proper alignment with axis 14. The result is a polarization current flow 27 within the dielectric resonator 12 (shown in FIG. 2) oscillating circumferentially about axis 14 at the resonant frequency of the dielectric resonator 12.

Figure 3:
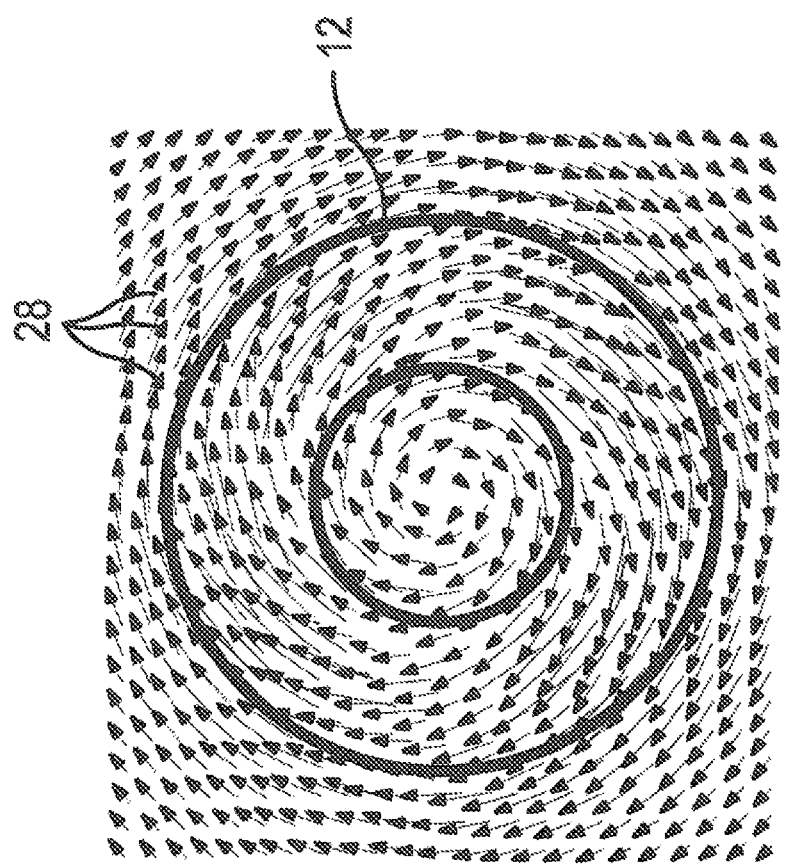
FIG. 3 is a model showing the electrical field in the ring dielectric resonator of FIG. 2.

Referring now to FIG. 3, the electric field 28 within the dielectric resonator 12 at a given instant in time is substantially tangential to the inner and outer circumferential peripheries of the dielectric resonator 12 representing a purely inductive field where parasitic capacitive coupling has been substantially eliminated. The electric field 28 is believed to be of such a high quality because the dielectric resonator is at once its own capacitor and an inductor and therefore electric-potential is exactly zero everywhere inside the dielectric resonator 12 and in the space around the dielectric resonator 12.

Referring again to FIG. 1, a gas source 32, for example, argon for an argon-based plasma may be provided through a regulator 34 to a gas port 36 directing gas along axis 14 through the center of the dielectric resonator 12. Within the dielectric resonator 12, the high electrical fields convert the gas to a plasma 40 that may flow along axis 14. The distance of flow is determined by the lifetime of the plasma excitation. The dielectric resonator 12 may be placed in a radiofrequency shield 42 to reduce power loss due to radiation of electromagnetic energy, minimize human exposure to high intensity non-ionizing radiation and control electromagnetic interference. The shield 42 may be connected to the return of the coaxial cable 22.

The use of the dielectric resonator 12 instead of a conductive metallic multi or single loop coil directly driven by an amplifier provides multiple benefits including:

a) Energy losses in the dielectric resonator 12 are one to two orders of magnitude lower than the conduction losses in a conventional coil. In many applications, this may completely eliminate the need for fluid cooling, greatly reducing the size, cost, and complexity of the plasma source. In semiconductor processing applications, it may be possible to eliminate the need for environmentally damaging dielectric cooling fluids.

b) The extremely low energy losses in the dielectric resonator 12 translate into a very large electric field strength during the plasma ignition phase, when no power is absorbed by the plasma. This makes for easier and more reliable ignition of the plasma discharge.

c) The self-resonant nature of a dielectric resonator 12 greatly simplifies or eliminates the need for an external impedance matching network between the dielectric resonator 12 and the power supply 18, thus reducing the size, cost, and the complexity of the plasma source.

d) The use of ceramic materials, such as alumina, in the dielectric resonator 12 provides a plasma generator compatible with ultra-high-vacuum processes that can be placed directly inside a vacuum chamber in order to improve the coupling to the plasma or to accommodate limited space available for the plasma source.

e) Creating the dielectric resonator 12 from ceramic materials, such as alumina which have high thermal conductivity, allows for rapid heat removal by conduction. If the dielectric resonator 12 is in direct contact with plasma, this can enable an efficient cooling of the plasma gas, a particularly important feature in gas-discharge laser applications.

f) The use of ceramic materials, such as alumina for the dielectric resonator maintains good mechanical and electric characteristics at extremely high temperatures in excess of 1,000 degrees Centigrade, which makes a dielectric resonator 12 well suited to applications involving high-temperature atmospheric plasma.

g) Pure inductive field, extremely low losses, high-temperature operation, and high thermal conductivity, possible with the present design, all enable operation at power levels well in excess of what is possible today with the conventional inductively coupled plasma technology.

Figure 4:
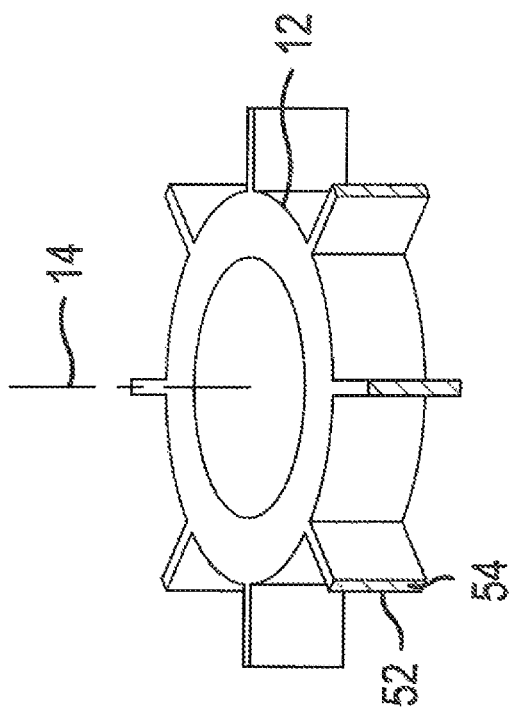
FIG. 4 is a perspective view of an alternative embodiment of a ring dielectric resonator having standoffs for thermal conduction path to a supporting structure and airflow.

Referring now to FIG. 4, in an alternative configuration dielectric resonator 12 may provide for radially extending standoffs 52 that may, for example, support the dielectric resonator 12 against a supporting structure such as a tubular shield 42 shown in FIG. 1. The ends of the standoffs 54 may be plated with a metal in order to reduce thermal resistance to a metal enclosure to assist in cooling of the dielectric resonator 12 which may also be cooled by natural convection or forced flow of air around the standoffs 52.

Figure 5:
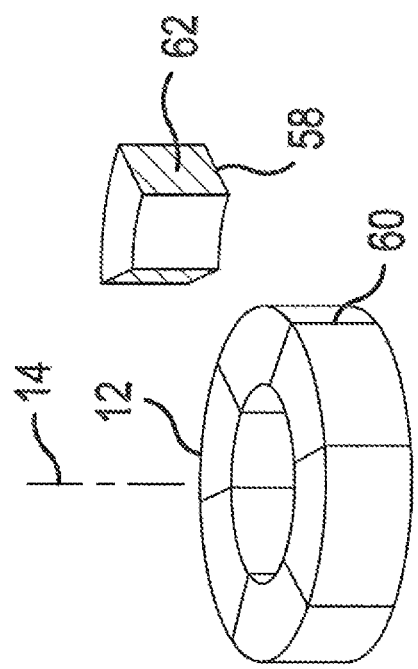
FIG. 5 is a perspective view of a ring dielectric resonator fabricated of individual sectors and showing one such sector.

Referring now to FIG. 5, particularly for larger dielectric resonators 12, the dielectric resonator 12 may be assembled from multiple annular sectors 58 placed together at seams 60 being an abutment of metal plated end surfaces 62. The small amount of non-dielectric material does not significantly impact the benefits of the dielectric.

Figure 6:
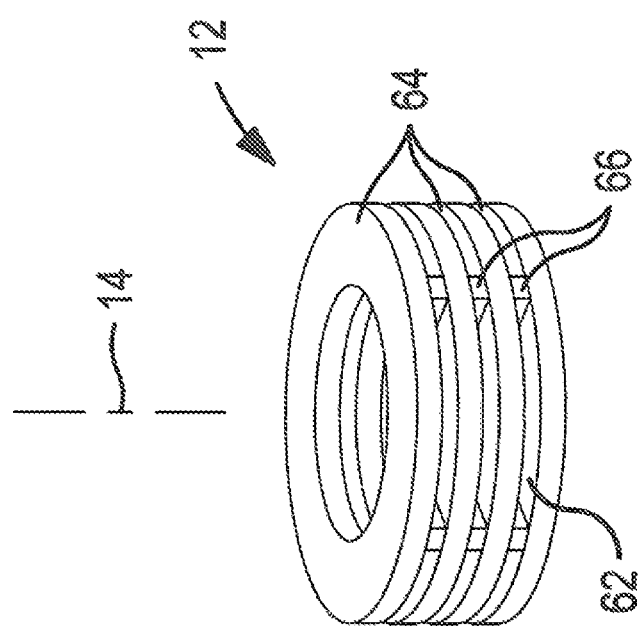
FIG. 6 is a perspective view of a dielectric resonator fabricated from multiple laminated rings.

Referring now to FIG. 6, the dielectric resonator 12 may be constructed out of multiple thin rings 64 aligned along common axis 14 held apart by thin insulating spacers 66. Smaller rings may be easier to manufacture and transport and the gaps between the end surfaces 62 may provide improved cooling while preventing undesirable flow of dielectric polarization currents in the axial direction.

Figure 7:
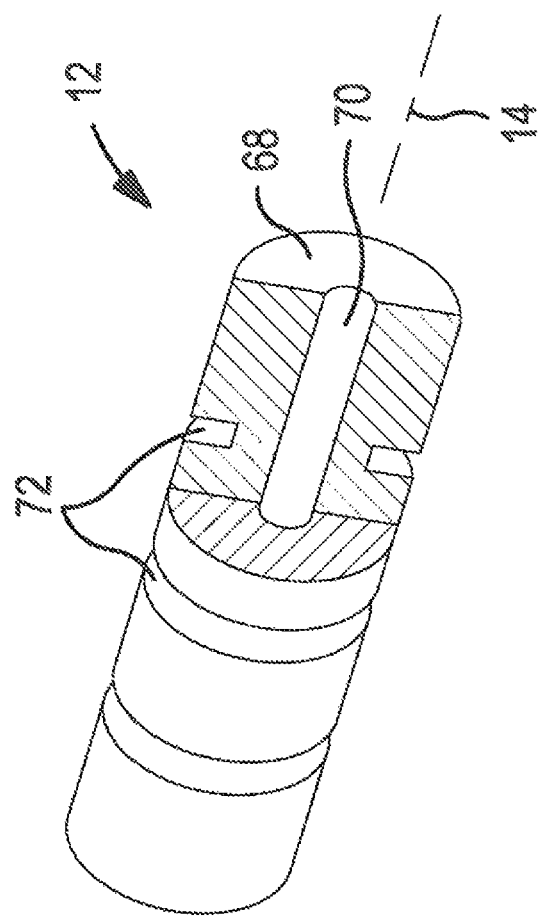
FIG. 7 is a perspective partial cutaway view of a dielectric resonator fabricated from a rod having circumferential grooves and a central axial bore.

Referring now to FIG. 7, a similar result may be achieved by fabricating the dielectric resonator 12 in the form of an elongated tube 68 having a central axial bore 70 and outer circumferential notches 72 serving to prevent axial polarization currents.

Figure 8:
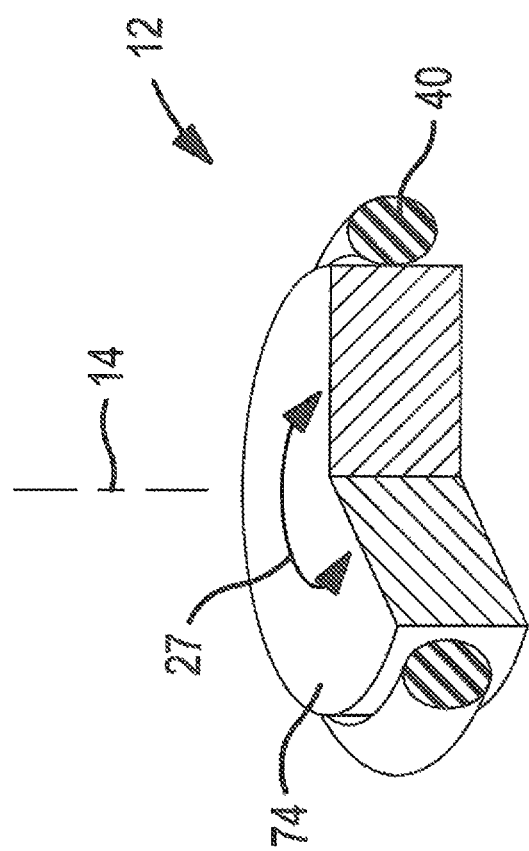
FIG. 8 is a perspective partial cutaway view of a disk dielectric resonator showing an external plasma region

Referring now to FIG. 8, it will be appreciated that the dielectric resonator 12 need not be a ring but that a toroidal plasma 40 may be generated around the outer periphery of a dielectric resonator 12 in the form of a disk 74. The toroid of the plasma 40 may be centered about axis 14 being an axis of symmetry of the disk 74. Proper selection of the resonant mode ensures a primary circumferential current component in the resonance of the disk 74.

Figure 9:
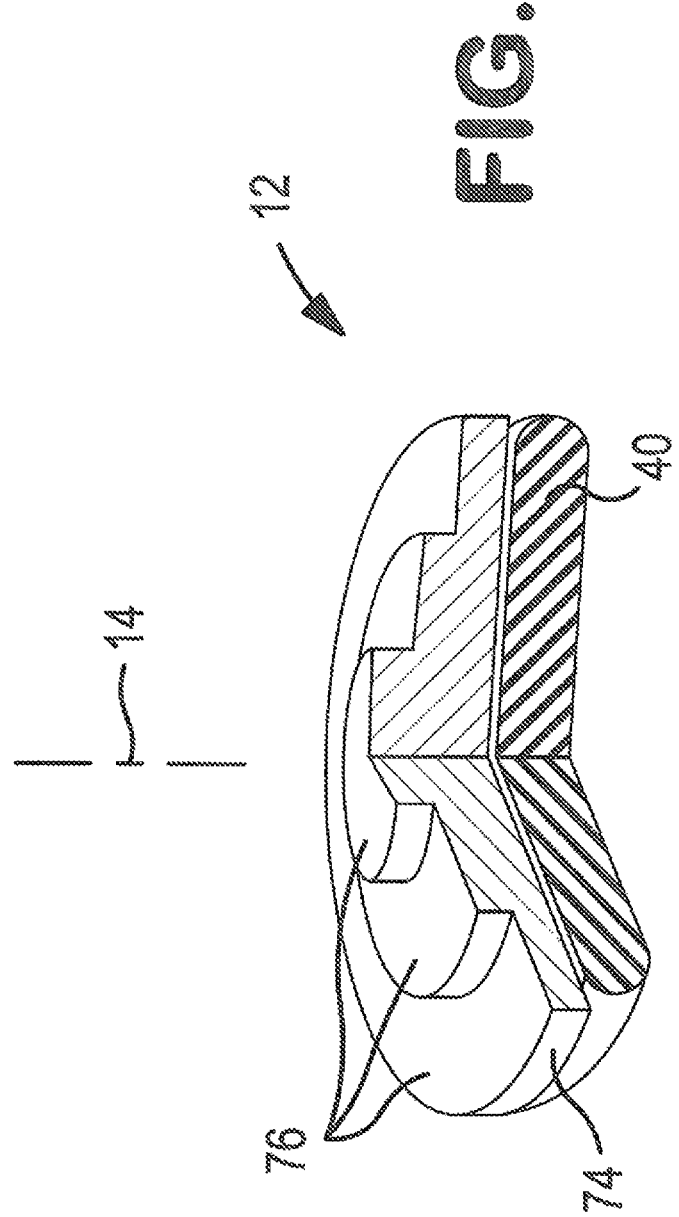
FIG. 9 is a perspective partial, cutaway view of a disk dielectric resonator providing a stepped surface disk to produce an axial disk-shaped plasma.

Referring now to FIG. 9, by establishing a series of circular steps 76 of increasing height as one moves toward the center of the disk 74, the plasma 40 may be displaced to an opposite face of the disk 74 of the dielectric resonator 12. The idea behind the steps 76 is to address the fact that in a simple ring or disk, the electric field is zero on the axis and increases nearly linearly towards the outer radius. The field and the plasma are most intense near the ring. The steps serve to increase the polarization current at smaller radii (by increasing the thickness) so that the induced electric field is more uniform between the axis and the outer radius. It is believed that this may improve radial plasma uniformity. As far as displacing the plasma is concerned, plasma on the other side of the disk would have to be suppressed by high-vacuum or higher gas pressure, for example.

Figure 10:
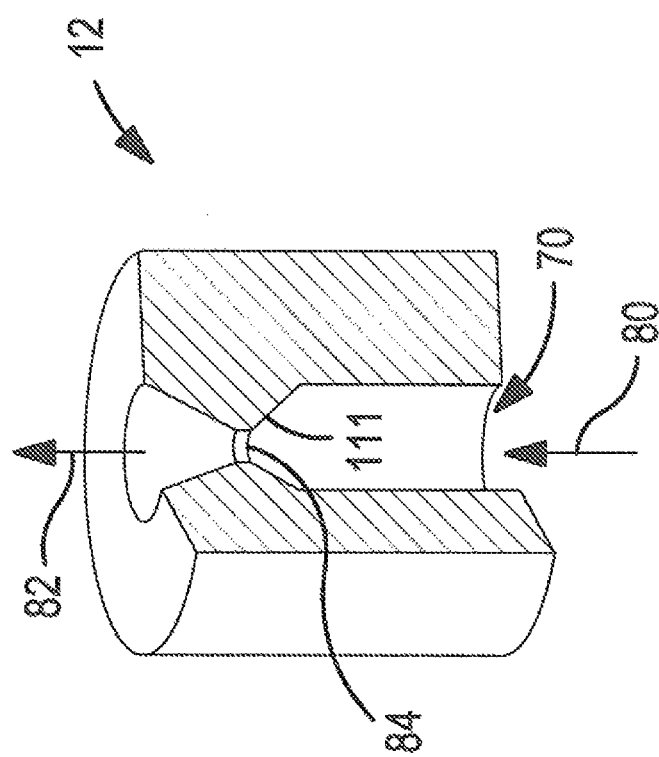
FIG. 10 is a perspective partial cutaway view of a nozzle for use in plasma cutting and welding or plasma thrusters.

Referring now to FIG. 10, in one embodiment the dielectric resonator 12 may provide for a convergent-divergent nozzle for the purpose of accelerating hot subsonic plasma flow 80 into supersonic plasma flow 82, in applications such as plasma cutting and welding or rocket engines. In this case, the dielectric resonator 12 includes a central bore 70 that neck inward to a smaller diameter 84, for example, to produce a de Laval nozzle at a point of plasma generation.

It will be appreciated that that many variants shown in the above Figs. may be combined in various ways. For example, the standoffs 52 of FIG. 4 can be combined with the rocket nozzle of FIG. 10 in order to facilitate heat removal, or the notches 72 shown in FIG. 7 can be implemented in the disks of FIGS. 8 and 9, in the form of circumferential grooves cut downward into one of the faces of the disk 74 to promote the desired current flow patterns.

Figure 12:
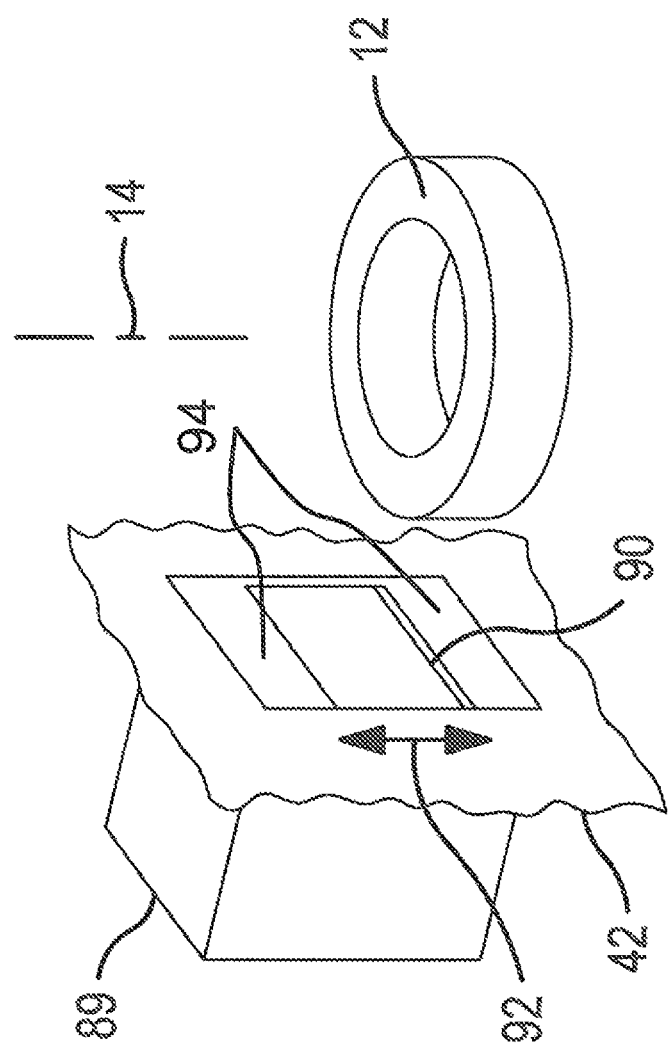
FIG. 12 is a figure similar to FIG. 11 showing a coupling system employing a microwave waveguide.

Referring now to FIG. 12, other methods of exciting the dielectric resonator 12 into resonance may be employed, for example, placing the dielectric resonator 12 at the end of a waveguide 89 directed generally perpendicular to the axis 14 driven by a microwave source. An opening 90 of the waveguide 89 may be controlled by an iris mechanism that may open and close iris 94 as indicated by arrows 92 to control the degree of coupling between the microwave source and the dielectric resonator 12

Figure 15:
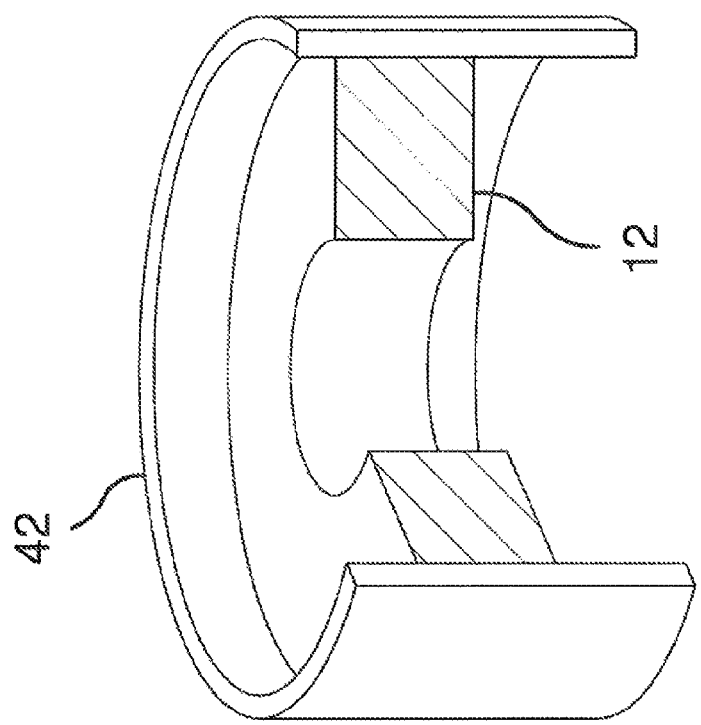
FIG. 15 is a perspective partial cutaway view of a dielectric resonator together with an RF shield in direct contact with an outer surface of the dielectric resonator.

Referring now to FIG. 15, the RF shield 42 may be in direct contact with an outer surface of the dielectric resonator 12. This configuration offers the advantage of smaller size and better transfer of heat to the RF shield 42. The surface of the ceramic ring 12 which is in contact with the RF shield 42 may be plated with metal.

Figure 16:
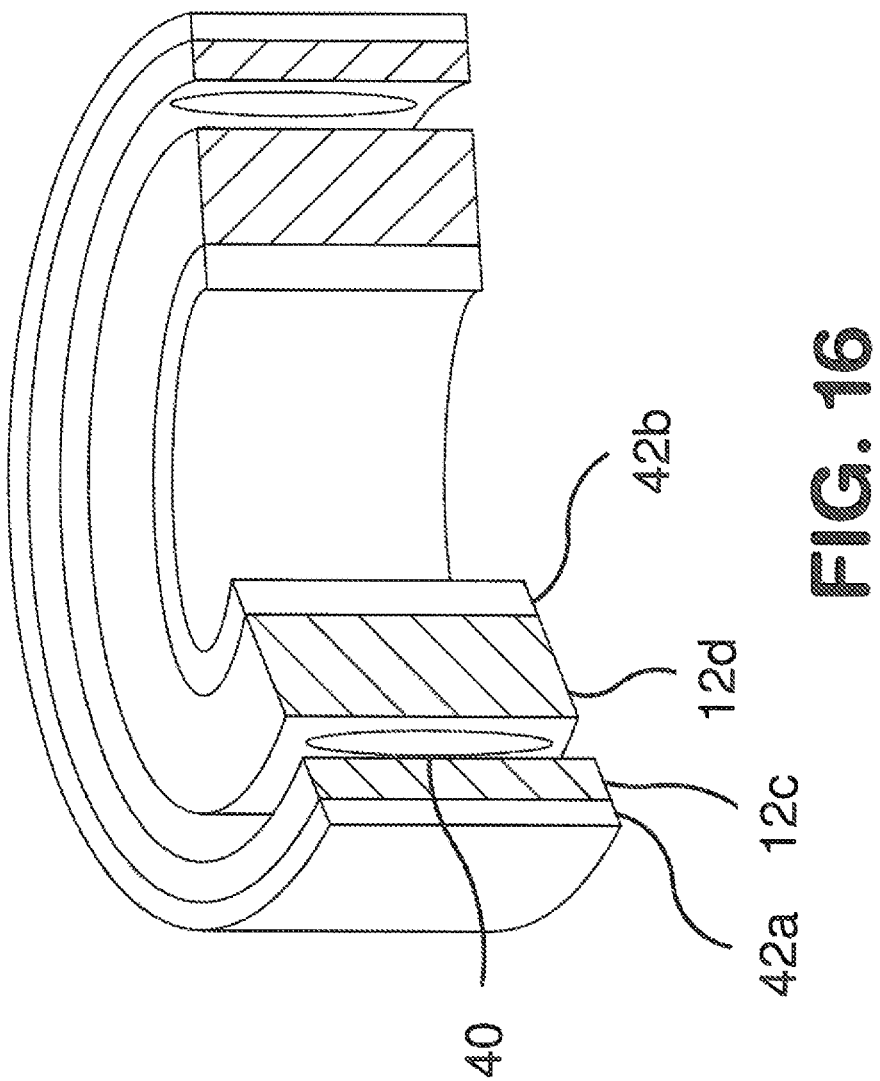
FIG. 16 is a perspective partial cutaway view of a dielectric resonator in the form of two coaxial ceramic rings, together with two RIF shields.

Referring now to FIG. 16, plasma 40 may be formed in the annular gap between two concentric ceramic rings 12*c* and 12*d*. The outer surface of the larger ring 12*c* is in direct contact with outer RF shield 42*a*. The inner surface of the smaller ring 12*d* is in direct contact with inner RF shield 42*b*. The annular gap between concentric rings 12*c* and 12*d* is preferably located at or near the radius where the electric field strength is the highest.

Example 1

Optical Emission Spectroscopy

The present invention may be used in an optical emission spectrometer (OES) where their purpose is to excite the atomic and molecular species in an unknown chemical sample and produce light. The spectroscopic analysis of the light emitted by the plasma is used to determine the type and quantity of the chemical substance present in the sample. Plasma properties critically affect the analytical performance of an OES, in terms of the ability to process samples in aqueous or organic solvents without extinguishing the plasma, the ability to operate on different plasma gases for improved safety and economy, the ability to detect different kinds of chemicals, the ability to accurately measure a very large range of analyte concentrations, the ability to detect extremely small concentrations of the analyte, the ability to process many samples in a short amount of time, the ability to produce stable results when measurements are repeated over a long period of time, etc.

Typical plasma sources for this application may operate at radio-frequencies up above 40 MHz with much higher frequencies implemented by this design. Alternatively, the design may provide plasma at microwave frequencies, such as 915 MHz or 2,450 MHz, using a magnetron device as a source of large amount of microwave power. Existing designs for plasma generators are dominated by capacitive coupling or retain a significant amount of parasitic capacitive coupling, which has a serious negative impact on the plasma source, or have form factors that would require significant modifications to the conventional mechanical, optical, and chemical interface to the rest of the spectrometer, an interface which has proven itself over many years of operation of radio-frequency OES in the field.

In contrast, the plasma source of the present design may extend the operation of the conventional radio-frequency inductively coupled plasma sources to microwave frequencies, practically eliminating parasitic capacitive coupling which has limited previous designs, while requiring minimum modifications to the established mechanical, optical, and chemical interface with the rest of the spectrometer. In addition, the extremely low losses of the novel field applicator, allow for a complete elimination of the fluid cooling system, thus reducing the size, cost, and the complexity of the spectrometer.

Referring now to FIG. 17 a microwave inductively coupled plasma source for optical-emission spectroscopy 102 uses a dielectric resonator 12 of the present invention, made out of high-density Alumina (Al2O3) ceramics in the form of a circular annulus. The dielectric resonator 12 may be supported within cylindrical radio-frequency shield 42 made of metal, such as aluminum, and has several circular openings 104, 106, and 108 each surrounded with aluminum tubular extensions 110, 112, and 114 respectively. The tubular extensions 110-114, are designed to have a sufficiently small diameter and sufficiently long length to form cylindrical waveguides below cutoff, greatly attenuating the propagation of microwaves through the extension tubes, as is well understood in the microwave art, in order to minimize the leakage of microwave energy outside of the shield 42.

Microwave power 118 from waveguide 89 communicating with magnetron 120 is provided at a frequency of 2,450 MHz and applied to the dielectric resonator 12 thru a rectangular opening 90 in the shield 42 by the means of a coupler 124. The resonant frequency of the dielectric resonator 12 can be finely adjusted by varying the axial location of the tuning element 44, made in the form of an aluminum ring, positioned coaxially with the ring of dielectric resonator 12.

A triaxial manifold 125 is directed along the axis 14 centered within opening 104 and aligned with inner diameter of dielectric resonator 12 and made out of quartz or alumina tubing. A plasma cooling gas 126 is applied to an outer ring of the triaxial manifold 125 while a plasma auxiliary gas 128 is applied to the next inner ring and the center bore receives the dissolved analytical sample 130 from a sample source 132 being analyzed. The sample 130 is in the form of an aerosol that may be directly introduced into the plasma 40.

Light 134 emitted from the plasma 40 in a direction radial to axis 14 passes through the tubular extension 112 for analysis by a light sensor 136 coupled to an analyzing computer 138 that may determine frequency components of the light 134 according to methods known in the art. Alternatively or in parallel, for the purposes of the, so called, axial OES, light 140, emitted by the plasma 40 in the axial direction of axis 14, is transferred through the tubular extension 110 for further spectroscopic analysis by a similar light sensor 136 (not shown for clarity). The tubular extension 110 also directs the hot plasma gases and chemical products 142 to an exhaust venting system (not shown.) The opening 108 and the tubular extension 114 allow for air cooling of the plasma generator 12 by natural convection or by forced flow of air.

Example 2

Mass Spectroscopy

The present invention offers similar advantages in both optical emission and mass spectroscopy (MS), with the added advantage in mass spectroscopic applications of an improved control over ion velocities, increased ion collection efficiency, and reduced sputtering of the sampler cone.

Referring now to FIG. 18, a microwave inductively coupled plasma source for mass spectrometry 200 uses a field applicator 12 of the present invention, made of high-density Alumina (Al2O3) ceramic in the form of a ring. The microwave inductively coupled plasma source for MS 200 has many components, in common with the microwave inductively coupled plasma source for OES 102 shown in FIG. 17, and like components have the same identifiers. Additional components shown in FIG. 18 will now be described. The sampler cone 201 has a small orifice 202 and the skimmer cone 203 has a small orifice 204. The region between the sample cone 201 and the skimmer cone 203 is maintained at a low pressure by exhausting the gas 205 by means of a vacuum pump (not shown). The ionized sample 206 enters the low pressure region between the sample and skimmer cones through the orifice 202. Ions 207 are further transmitted through the orifice 204 into the high-vacuum region of the mass-spectrometer. The mass spectrometer comprises ion focusing components 209 which comprise at least one ion focusing element, a mass analyser 210 and an ion detector 211. There may be two or more stages of pumping (not shown) disposed within the mass spectrometer. The mass spectrometer is controlled by a controller (not shown), which is preferably a computer. Detected signal from ion detector 211 is recorded, preferably also using a computer, which may be the same computer as is used as the controller. The heated plasma gas 208 which has not penetrated the orifice 202 is exhausted through the annular region between the RF shield 42 and the sample cone 201.

Example 3

Convection Cooled Microwave Gas Discharge Laser

A plasma generator of the present invention may be used to construct a compact, medium-power, gas-discharge laser producing a high-quality beam of several hundred Watts of optical power. The design is based on convection cooling and pure inductively coupled gas-discharge at a microwave frequency.

FIGS. 19a and 19b show a cross-section and a top view, respectively, of a medium power compact gas-discharge laser 300 based on the dielectric resonator 12 of the present invention. The dielectric resonator 12 is in the form of an elongated tube 68 with axis 14, having a central axial bore 70 and outer circumferential notches 72 (see FIG. 7.) Dielectric resonator 12 may be made of high density Alumina (Al2O3). A cylindrical RF shield 42 includes a plasma gas inlet 302 and a plasma gas outlet 304. Cold gas 306 enters through the gas inlet 302, flows through the central axial bore 70, and exits as a heated gas 308 through the gas outlet 304. Inlet 302 and outlet 304 are connected to a gas circulation system (not shown) which includes a blower and a heat exchanger for cooling the gas, as is well known in the art. Microwave power 118, such as provided by a 2,450 MHz magnetron (not shown), is coupled to the laser 300 by means of a waveguide port 124 in the RF shield 42 which has an opening 90 defined by a pair of irises 94. An inductively coupled plasma 40 is formed in the inner bore 70 of the dielectric resonator 12. Flat ends of the cylindrical shield 42 support a reflective spherical mirror 310 and a semi-transparent spherical mirror 312 which form an optical cavity. Plasma 40 is an optical gain medium inside the optical cavity formed by mirrors 310 and 312 and results in the emission of a high-quality axially symmetrical optical beam 314 of several hundred Watts which can be focused at a spot of very small size by suitable external optical components (not shown). The surfaces of the dielectric resonator 12 which are in contact with the metal shield 42 are preferably metal plated.

Example 4

Diffusion Cooled Coaxial Microwave Gas Discharge Laser

A plasma generator of the present invention may be used to construct a high-power gas-discharge laser of scalable design, capable of producing high quality optical beam with an optical power of several kilowatts. The optical design adopts a coaxial, diffusion-cooled configuration which is well known in the art. Diffusion lasers do not require a blower and consume minimal amount of gas. However, while the plasma in a conventional coaxial laser is sustained by a pure capacitive RF discharge between inner and outer coaxial electrodes, which sets a power limit due to discharge instabilities inherent in capacitive coupled plasma, the present invention uses an inductively coupled plasma to obtain a stable discharge at higher power level while at the same time operating at a microwave frequency where high power magnetrons can be used as more convenient, compact, and efficient power sources. In addition, due to the high the mal conductivity of the ceramic field applicator which is in direct contact with the laser gas, the effectiveness of the diffusion cooling is preserved.

Figure 20:
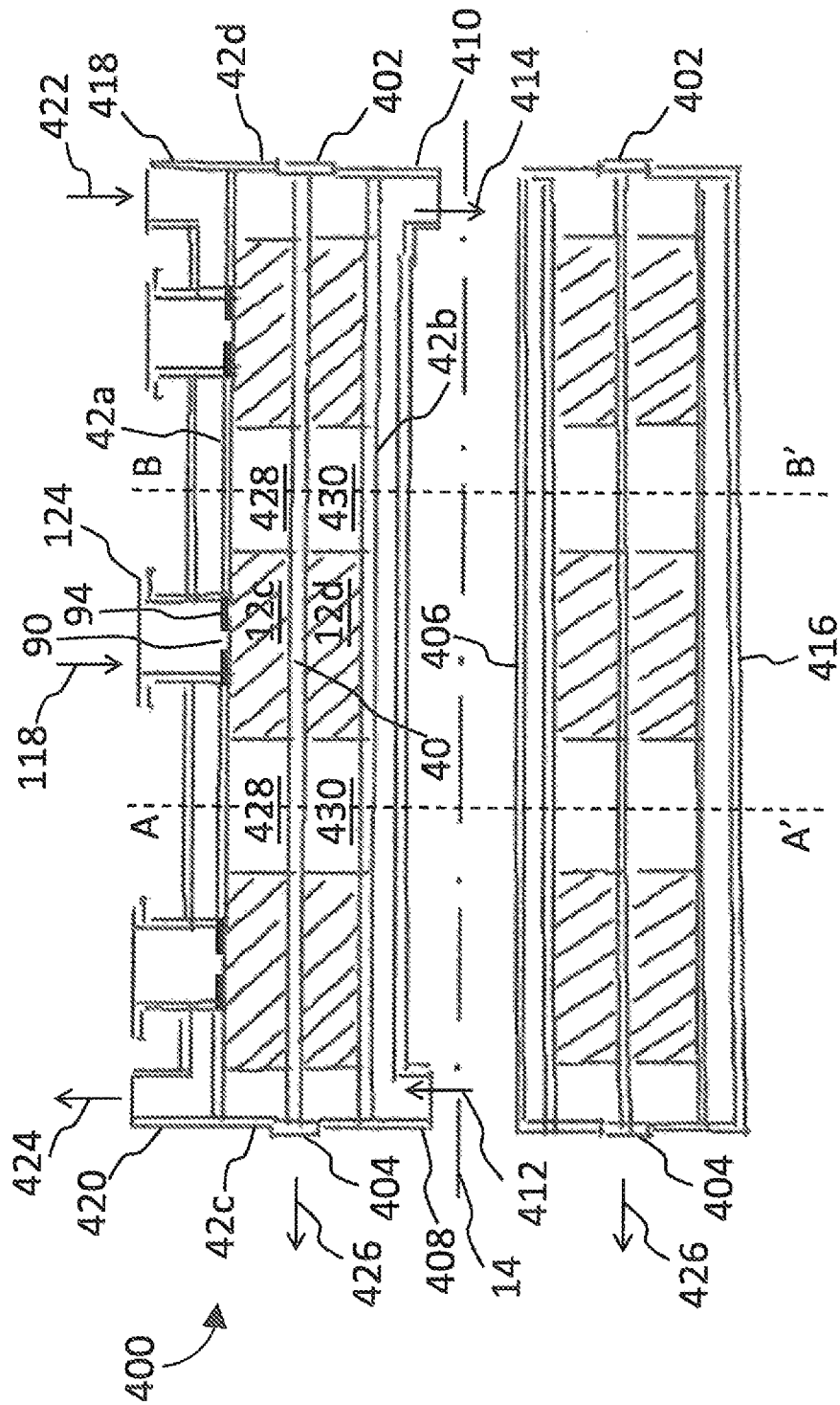
FIG. 20 is a simplified cross-sectional view of a diffusion cooled coaxial microwave gas discharge laser according to the present invention

FIG. 20 shows a cross-section of a high-power diffusion-cooled coaxial laser 400 using a dielectric resonator of the present invention in the form of ceramic rings 12c and 12d. A cylindrical RF shield consists of a larger diameter metal tube 42a and a smaller diameter metal tube 42b with a common axis 14. The space between the tubes 42a and 42b is hermetically sealed by flat end-plates 42c and 42d and filled with a lasing gas, such as a mixture of carbon-dioxide ($CO_2$), nitrogen ($N_2$), and helium (He). A reflective toric mirror 402 and a semi-transparent toric mirror 404 are mounted on plates 42d and 42c, respectively, and form a coaxial optical cavity. The inner RF shield 42b is surrounded by a water jacket 406 which includes a water inlet 408 and a water outlet 410. Cold water 412 enters the inlet 408 and the heated water 414 is removed through the water outlet 410. The outer RF shield 42a is surrounded by a water jacket 416 which includes water inlet 418 and a water outlet 420. Cold water 422 enters the inlet 418 and the heated water 424 is removed through the outlet 420. Parts shown between sections AA' and BB' form a modular assembly that can be repeated in the axial direction 14 one or more times to increase the output beam power of the laser. One of 3 such identical modules shown in FIG. 18 will now be described. Outer RF shield 42a also includes waveguide ports 124 with openings 90 defined by pans of irises 94. Microwave power 118 can be supplied to each of the waveguide ports 124 by a separate microwave source (not shown), such as from high-power 915 MHz or 2,450 MHz magnetrons normally used for industrial heating applications. Dielectric resonator consists of two rings, the outer ring 12c and the inner ring 12d, made from a ceramic material such as high density Alumina ($Al_2O_3$). The gap between the outer surface of the inner ring 12d and the inner surface of the outer ring 12c is only a few millimeters wide in order to enable an effective transfer of heat by thermal diffusion from the gas to the ceramic rings 12c and 12d. High thermal conductivity of the ceramic rings rapidly transfers the heat from the plasma gas to the water flowing inside the cooling jackets 406 and 416. Plasma 40, sustained by a pure inductive coupling, forms an optical gain medium inside the optical cavity formed by toric mirrors 402 and 404. This results in the mission of a high-power, cylindrically symmetric, high quality coaxial optical beam 426 which, as is well known in the art, can be focused by external optical components (not shown) to a spot of small size. Metal rings 428 and 430 serve to minimize the inductive coupling between the modules and to facilitate the diffusive transfer of heat from the gas to the water flowing inside the cooling jackets 406 and 416. If the thickness of the ring is defined as the difference between the outer and the inner radius of the ring, FIG. 20 shows both rings 12c and 12d as having approximately identical thickness. However, the present invention is not limited to rings of equal thickness.

Example 5

Convection Cooled Coaxial Microwave Gas Discharge Laser

A plasma generator of the present invention may be used to construct a very-high-power gas-discharge laser of scalable design, capable of producing high quality optical beam with a power of tens of kilowatts. The design adopts a coaxial, convection-cooled configuration which is well known in the art. However, while the plasma in a conventional coaxial laser is sustained by a pure capacitive RF discharge between inner and outer coaxial electrodes, which sets a power limit due to discharge instabilities inherent in capacitive coupled plasma, the present invention uses an inductively coupled plasma to obtain a stable discharge at higher power level while at the same time operating at a microwave frequency where high power magnetrons can be used as more convenient, compact, and efficient power sources.

Figure 21:
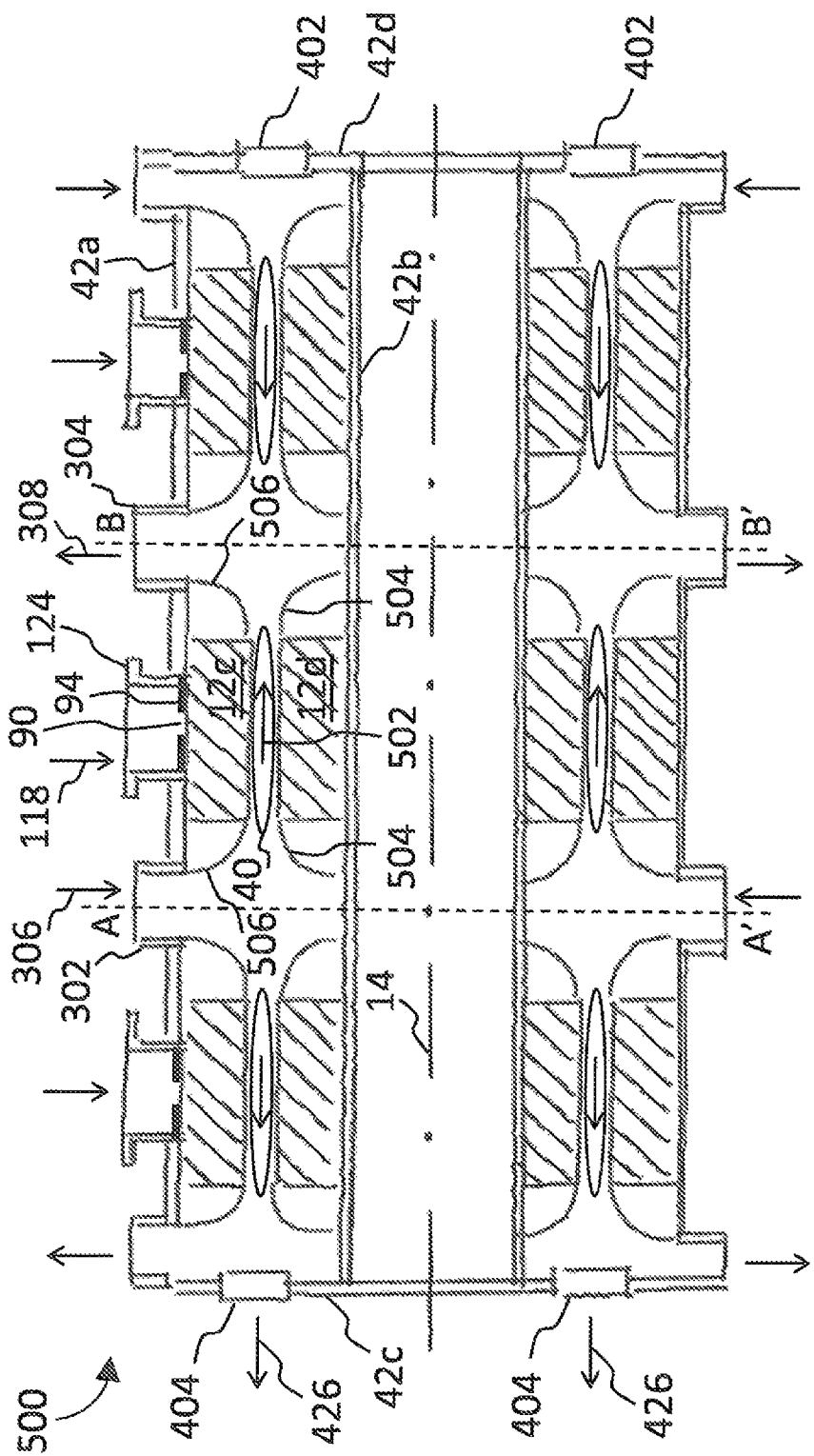
FIG. 21 is a simplified cross-sectional view of a convection cooled coaxial microwave gas discharge laser according to the present invention

FIG. 21 shows a cross section of a convection cooled inductively coupled coaxial gas discharge laser 500 using a dielectric resonator of the present invention in the form of ceramic rings 12c and 12d. The RF shield is formed by an outer metallic tube 42a and an inner metallic tube 42b with a common axis 14. The space between the tubes 42a and 42b is hermetically closed with flat plates 42c and 42d, which support a reflective toric mirror 402 and a semi-transparent toric mirror 404. Mirrors 402 and 404 form a coaxial optical cavity, as is well known in the art of high power gas discharge lasers. Parts shown between sections AA' and BB' form a modular assembly that can be repeated in the axial direction 14 one or more times to increase the output beam power of the laser. One of 3 such identical modules shown in FIG. 19 will now be described. The outer RF shield 42a is provided with gas inlets 302 and outlets 304. Cold plasma gas 306 enters the laser 500 through the inlet 302 and the heated plasma gas 308 leaves through the outlet 304. Inlets 302 and outlets 304 are connected to a gas circulation system (not shown) which includes a very high flow-rate blower and a heat exchange system for cooling the gas, as is well known in the art. The direction of the gas flow is indicated by arrows 502. The outer RF shield 42a also includes waveguide ports 124 with openings 90 defined by pairs of irises 94. Microwave power 118 can be supplied to each of the ports 124 by a separate microwave source (not shown), such as from high-power 915 MHz magnetrons normally used for industrial microwave heating applications. Dielectric resonator consists of two rings, the outer ring 12c and the inner ring 12d, made from a ceramic material such as high density Alumina (Al2O3). The gap between the outer surface of the inner ring 12d and the inner surface of the outer ring 12c is approximately 1 to 2 cm wide to provide sufficient cross-sectional area for the high flow-rate of the plasma gas for heat removal purposes. Plasma 40, sustained by pure inductive coupling, forms an optical gain medium inside the optical cavity formed by toric mirrors 402 and 404. This results in the emission of a very high power, cylindrically symmetric, high quality coaxial optical beam 426 which, as is well known in the art, can be focused by external optical components (not shown) to a spot of small size. Metal rings 504 and 506 with a rounded edge have a three-fold purpose: to confine the electromagnetic field to the region occupied by the rings 12c and 12d, to minimize the inductive coupling between adjacent modules, and to help guide the high-speed flow of plasma gas 306 and 308. The surfaces of the ceramic rings 12c and 12d which are in contact with metal shields 42a and 42b and metal rings 504 and 506 are preferably metal plated. If the thickness of the ring is defined as the difference between the outer and the inner radius of the ring, FIG. 21 shows both rings 12c and 12d as having approximately identical thickness. However, the present invention is not limited to rings of equal thickness.

Example 6

Electron-Cyclotron-Resonance Plasma Source

A plasma generator of the present invention may be used to construct an electron-cyclotron-resonance plasma source. The source may be used for plasma processing of semiconductor wafers, as an ion source, or as an ion-thruster for in-space propulsion.

Figure 22:
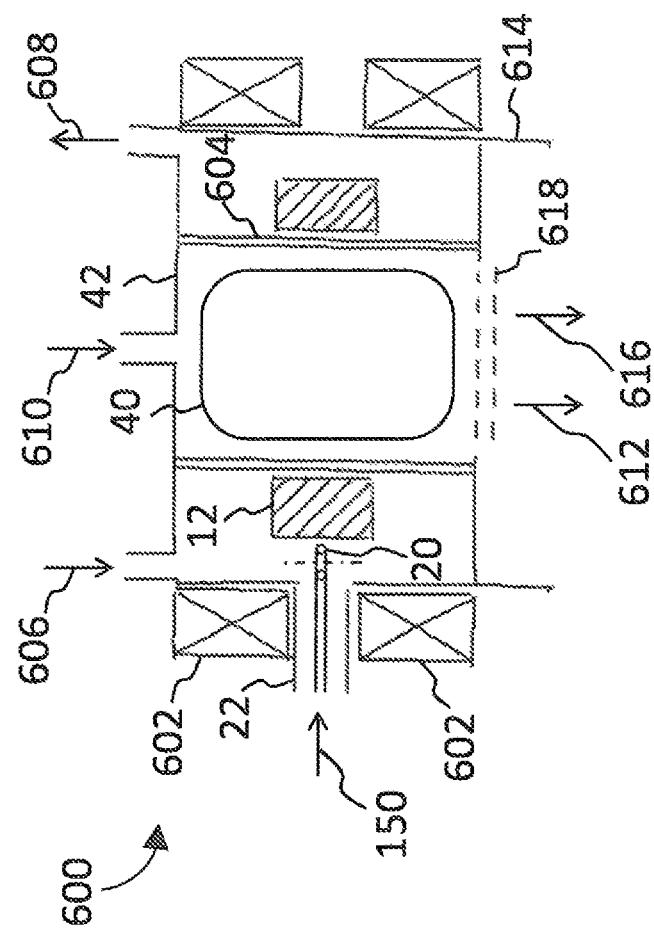
FIG. 22 is a simplified cross-sectional view of an electron-cyclotron resonance plasma source using the teachings of the present invention.

FIG. 22 shows an electron-cyclotron-resonance plasma source 600 using a dielectric resonator 12 of the present invention in the form of a ring. Dielectric resonator 12 is made from an advanced technical ceramics material, such as calcium-titanate (CaTiO3) ceramics, having a large relative dielectric constant and very low dielectric losses. A cylindrical RF shield 42, made from a non-magnetic material, such as stainless steel, is surrounded by a set of electromagnets or permanent magnets 602 in order to create a static magnetic field suitable for the production of electron-cyclotron-resonance (ECR) plasma, as is well known in the art of ECR plasma sources. Radio-frequency power 150 is supplied through a coaxial transmission line 22 terminated by a coupling loop 20. One end of the coupling loop 20 is connected to the center conductor of the coaxial cable 22 and the other end of the loop is connected to the RF shield 42. Quartz tube 604 and RF shield 42 form a gas tight enclosure such that the space inside the quartz tube 604 can be maintained at low pressure while the rest of the plasma source is at atmospheric pressure. Cold air or cooling fluid 606 removes the heat from the field applicator 12, quartz tube 604, and the RF shield 42, and is exhausted as heated air or fluid 608. Low pressure plasma gas 610 enters the quartz tube 604 where it is converted to plasma 40. Plasma is sustained by the combined action of a pure inductive RF field of the field applicator 12 and the static magnetic field of the electro or permanent magnets 602. Spent gas 612 is removed by the action of a vacuum pump (not shown) connected to the vacuum vessel 614. In ion-thrusters for in-space propulsion, the vessel 614 would be replaced by a vacuum of interplanetary space. Ions 616 are extracted from plasma 40 by a system of grid electrodes 618, held at various electrostatic potentials by external DC power supplies (not shown), as is well known in the art of ion sources.

The preceding description of the ECR plasma source 600 shown in FIG. 22 assumes an excitation 150 in the form of RF energy. However, the dielectric resonator 12 of the present invention may be adopted for operation over a broad range of frequencies. For example, by changing the material of the field applicator 12 to high-density Alumina (Al2O3), the ECR plasma source of FIG. 22 could be made to operate at a microwave frequency, provided that the static magnetic field of electromagnets 602 is increased proportionally to the frequency. Optionally, for operation at microwave frequencies, coaxial cable 22 and the loop coupler 20 may be replaced by a waveguide and an iris coupler, respectively.

The primary function of the ECR plasma source 600 shown in FIG. 22 as a source of ions 616 has been chosen for illustrative purposes only. By removing the grid electrodes 618 and allowing a direct penetration of plasma 40 into the vacuum vessel 614, it becomes possible to use the ECR plasma source 600 for many other applications, such as chemical-vapor-deposition, plasma etching, plasma ashing, vacuum ion pumps, etc.

In some applications it may be advantageous to operate the plasma source 600 shown in FIG. 22 without electromagnets 602. Although in such a case there will be no enhancement of the plasma density by an ECR effect, the high efficiency and pure inductive coupling of the field applicator 12 of the present invention would still enable the production of high-density uniform plasma 40 superior to the conventional RF inductively coupled sources.

Example 7

Large Area, High-Density, Uniform Plasma Source

A plasma generator of the present invention may be used to construct a high-density, uniform plasma source suitable for processing of semiconductor wafers.

Figure 23:
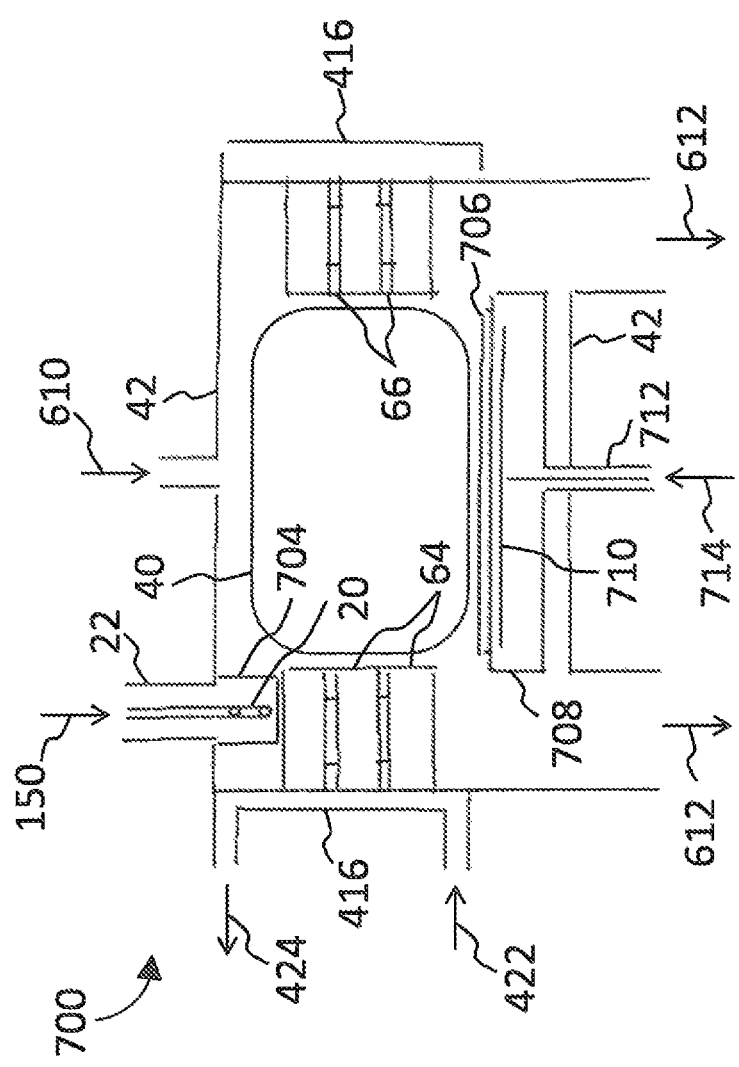
FIG. 23 is a simplified cross-sectional view of a large area, high-density, uniform plasma source according to the present invention.

FIG. 23 shows a plasma source 700 using a dielectric resonator of the present invention made in the form of a stack of one or more ceramic rings 64, held apart by spacers 66. Cylindrical RF shield 42 has a cooling water jacket 416. Cold water 422 removes the heat from the RF shield 42 and heated water 424 carries it to the chiller (not shown) which is part of a closed cooling system. Since the cooling water comes in contact only with the grounded RF shield 42, there is no need to use environmentally damaging dielectric cooling fluids as would be required when cooling the coil of a conventional inductively coupled plasma source. The heat generated inside the RF shield 42 is conducted to the walls of the RF shield by highly thermally conductive ceramic material of the dielectric resonator rings 64 whose outer cylindrical surface is in direct contact with the RF shield 42. RF power 150 is applied through a coaxial transmission line 22 terminated by a loop coupler 20 which is protected from the harsh plasma environment by a quartz or ceramic cap 704 which forms a gas tight fit with the RF shield 42. Low pressure plasma gas 610 is excited to plasma 40 by the action of the stack of dielectric resonators 64 and spent gas 612 is removed by a turbo-molecular vacuum pump (not shown.) Plasma 40 facilitates plasma processing of a semiconductor wafer 706 held on a chuck 708. The chuck 708 may contain an RF bias electrode 710 supplied by a coaxial transmission line 712 with RF power 714 which is generally at a different frequency form the RF power 150 used to sustain the plasma.

Example 8

Very Large Area, High-Density, Uniform Plasma Source

A plasma generator of the present invention may be used to construct a high-density plasma source producing uniform plasma over a very large area, suitable for processing of large semiconductor wafers and solar panels.

Figure 24:
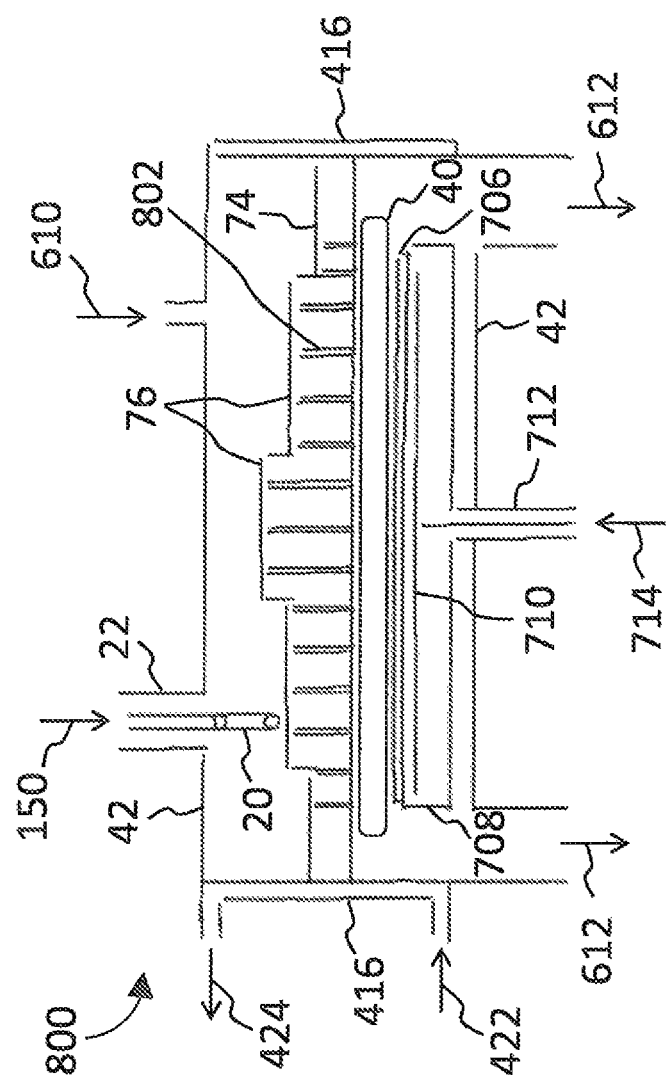
FIG. 24 is a simplified cross-sectional view of a very large area high-density, uniform plasma source according to the present invention.

FIG. 24 shows a plasma source 800 using the dielectric resonator of the present invention in the form of a ceramic disk 74 with steps 76 of variable thickness. The thickness of steps 76 may be optimized to obtain a radial distribution of dielectric polarization currents inside the dielectric which results in the most uniform plasma 40. Cylindrical RF shield 42 has a cooling water jacket 416. Cold water 422 removes the heat from the RF shield 42 and heated water 424 carries it to the chiller (not shown) which is part of a closed cooling system. The heat generated inside the RF shield 42 is conducted to the walls of the RF shield by highly thermally conductive ceramic material of the dielectric resonator 74 whose outer cylindrical surface is in direct contact with the RF shield 42. RF power 150 is applied through a coaxial transmission line 22 terminated by a loop coupler 20. Plasma gas 610 is admitted to the space above the disk 74 and flows through narrow capillary holes 802 evenly distributed across the surface of the disk 74, creating a showerhead effect. Due to the pressure drop across the narrow holes, pressure above the disk 74 is sufficiently high such that no plasma forms in this part of the plasma source 800. Plasma gas 610 flowing out of the bottom of the disk 74 is excited to a large-area, high-density, uniform plasma 40 and the spent gas 612 is removed by a turbo-molecular vacuum pump (not shown.) Plasma 40 facilitates plasma processing of a large diameter semiconductor wafer or a solar panel 706 held on a chuck 708. Chuck 708 may contain an RF bias electrode 710 supplied by a coaxial transmission line 712 with RF power 714 which is generally at a different frequency form the RF power 150 used to sustain the plasma.

Example 9

Microwave Plasma Torch

A plasma generator of the present invention may be used to construct electrode-less atmospheric plasma torches powered by inductively coupled microwave energy. Such torches may be used in advanced manufacturing, environmental, chemical synthesis, space, and scientific applications.

FIG. 25 shows an atmospheric microwave plasma torch 850 based on the plasma source using dielectric resonator 12 of the present invention. A cylindrical RF shield 42 is surrounded by a water cooling jacket 416 with an inlet for cold water 422 and outlet for heated water 424. Dielectric resonator 12 is made in the form of a ceramic ring whose outer cylindrical surface is in direct contact with the RF shield 42 for efficient removal of heat. RF shield 42 also includes waveguide port 124 with opening 90 defined by a pair of irises 94. Microwave power 118 can be supplied to the waveguide port 124 from a magnetron (not shown) A triaxial manifold 852, made of Alumina ceramics or quartz, guides the cooling gas 854, the auxiliary gas 856, and the particles of the material to be sprayed 858, thru the center opening of the dielectric resonator ring 12. High-temperature atmospheric pressure plasma 40 melts the material 858, creating a spray of molten material 860 which is implanted or deposited onto the surface of the object 862 undergoing surface treatment. As is well known in the art of atmospheric plasma torches, plasma-spraying application shown in FIG. 23 is only one of many possible applications which may be realized by using different substances 858 and objects 862 undergoing high-temperature plasma treatment.

FIG. 26 shows microwave plasma torch 870 based on a dielectric resonator 12 with a central bore 70 that necks inward to a smaller diameter 84, to form a convergent-divergent nozzle 111. A cylindrical RF shield 42 is surrounded by a water cooling jacket 416 with an inlet for cold water 422 and outlet for heated water 424. The outer surface of the dielectric resonator 12 is in a direct contact with the RF shield 42 for an efficient transfer of heat. RF shield 42 also includes waveguide port 124 with opening 90 defined by a pair of irises 94. Microwave power 118 can be supplied to the waveguide port 124 from a magnetron (not shown.) A biaxial manifold 872, made of Alumina or quartz, guides the cooling gas 854 and the plasma gas 874 into the central bore 70. Plasma gas 874 is converted to plasma and heated to high temperature by the absorption of microwave energy 118, thus forming a high-temperature subsonic flow 80. Large thermal energy of the subsonic flow 80 is converted to the kinetic energy of the supersonic flow 82 by the action of a convergent-divergent nozzle 111. Supersonic flow 82 can be used in advanced manufacturing applications, such as plasma welding and cutting, as well as in thermal rockets for in-space propulsion.

Example 10

Ion Cyclotron Resonance Plasma Heating

A plasma generator of the present invention may be used to construct an ion-cyclotron heating (ICRH) antenna for applications such as fusion reactors or variable-specific-impulse magnetoplasma rocket (VASIMR) for in-space propulsion.

FIGS. 27a and 27b show cross-sections A-A and B-B, respectively of a tokamak fusion reactor 900 using dielectric resonators 12 of the present invention. Vacuum vessel 42 also serves as an RF shield and is surrounded by superconducting electromagnets 902 which create a toroidal static magnetic field for the magnetic confinement of plasma 40. Dielectric resonator 12 is made in the form of a ring, from a dielectric ceramic material with a large relative dielectric constant. RF power 150 of the order of millions of Watts at a frequency between 10 MHz and 100 MHz, typical of ICRH, is supplied through a coaxial transmission line 22 terminated by a loop coupler 20 located inside a cavity 904 which forms the part of the RF shield 42.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

The term "ring" should be understood to generally mean a topological surface of genius one and not require nor exclude, for example, a circular profile, radial symmetry or particular aspect ratios of with a diameter to height except as explicitly noted.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A plasma generator comprising:
 a dielectric resonator structure having a central axis;
 a radiofrequency power source electrically coupled to the dielectric resonator structure to promote an alternating polarization current flow at a natural resonant frequency of the dielectric resonator structure about the axis to generate plasma in an adjacent gas.

2. The plasma generator of claim 1 wherein the dielectric resonator has a quality factor of greater than 100.

3. The plasma generator of claim 1 wherein the dielectric resonator has electrical resistivity greater than $1 \times 10^{10}$ $\Omega \cdot$cm.

4. The plasma generator of claim 1 wherein the dielectric resonator has a melting point greater than a melting point of copper.

5. The plasma generator of claim 1 wherein dielectric resonator has a dielectric constant with a loss tangent of less than 0.01.

6. The plasma generator of claim 1 wherein the dielectric resonator has a dielectric constant of greater than five.

7. The plasma generator of claim 1 wherein the material of the dielectric resonator is selected from the group consisting of alumina ($Al_2O_3$) and calcium titanate ($CaTiO_3$).

8. The plasma generator of claim 1 wherein the dielectric resonator is a ring having a central opening along the axis.

9. The plasma generator of claim 8 wherein the ring has a central opening of at least one millimeter in diameter or at least one half inch in diameter.

10. The plasma generator of claim 8 further including a gas port introducing gas into the ring along an axis of the ring.

11. The plasma generator of claim 1 further including a feedback system wherein the radiofrequency power source communicates with the feedback system to automatically seek the natural resonant frequency of the dielectric resonator structure to output radiofrequency power at the natural resonant frequency of the dielectric resonator structure.

12. The plasma generator of claim 1 wherein the radiofrequency power source is a magnetron.

13. The plasma generator of claim 1 wherein the radiofrequency power source output power in a range from 20 to 1000 megahertz.

14. The plasma generator of claim 1 wherein the radiofrequency power source outputs power in a range including at least one frequency selected from the group consisting of 13.56 MHz, 27 MHz, 40 MHz, 60 MHz, 430 MHz, 915 MHz, 2450 MHz.

15. The plasma generator of any of the preceding claims incorporated into of the structure of any single device in the group consisting of: an optical laser, a plasma torch, a rocket engine, an electron-cyclotron plasma or ion source, an inductively coupled plasma source for semiconductor processing, and an ion cyclotron plasma heater.

16. A method of generating plasma using a plasma generator including a dielectric resonator structure having a central axis and a radiofrequency power source electrically coupled to the dielectric resonator structure to promote an alternating polarization current flow at a natural resonant frequency of the dielectric resonator structure about the axis to generate plasma in an adjacent gas, the method comprising the steps of
 (a) introducing a gas into a region adjacent to the dielectric resonator structure; and
 (b) exciting the dielectric resonator structure at a natural resonant frequency to generate plasma in the introduced gas.

17. The plasma generator of claim 1 wherein the dielectric resonator is adapted in shape and material to primarily couple energy to the plasma inductively.

18. The spectrometer of claim 2 wherein axial surfaces of the dielectric resonator are substantially free from electrical shielding.

19. The plasma generator of claim 1 wherein the dielectric resonator and the radiofrequency power source are placed within a waveguide and the radiofrequency power source is electrically coupled to the dielectric resonator structure by radiation through the waveguide.

* * * * *